(12) United States Patent
Motley et al.

(10) Patent No.: US 11,771,566 B2
(45) Date of Patent: Oct. 3, 2023

(54) POROUS SPINAL IMPLANT

(71) Applicant: Zavation Medical Products, LLC, Flowood, MS (US)

(72) Inventors: Katie Lynn Motley, Flowood, MS (US); John Franklin Cummins, Kosciusko, MS (US); Joseph Matthew Jones, Madison, MS (US); John Lawrence Walker, Madison, MS (US); Colbert Yeates Williams, Brandon, MS (US)

(73) Assignee: Zavation Medical Products, LLC, Flowood, MS (US)

( * ) Notice: Subject to any disclaimer, the term of this patent is extended or adjusted under 35 U.S.C. 154(b) by 99 days.

(21) Appl. No.: 17/351,824

(22) Filed: Jun. 18, 2021

(65) Prior Publication Data

US 2021/0346169 A1    Nov. 11, 2021

Related U.S. Application Data

(63) Continuation of application No. 17/132,177, filed on Dec. 23, 2020, now Pat. No. 11,051,953, which is a
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/30771* (2013.01); *A61F 2/442* (2013.01); *A61F 2/4611* (2013.01); *A61F 2002/30807* (2013.01)

(58) Field of Classification Search
CPC .... A61F 2/44; A61F 2/447; A61F 2/46; A61F 2/4611; A61F 2/422; A61F 2/4455; A61F 2002/30807; A61F 2002/30771
(Continued)

(56) References Cited

U.S. PATENT DOCUMENTS 5,904,719 A    5/1999 Errico et al.
5,965,006 A *  10/1999 Baege ..................... A61L 27/34
                                                    205/685
(Continued)

OTHER PUBLICATIONS

Office Action for the U.S. Appl. No. 17/132,177 issued by the USPTO dated Feb. 18, 2021.
(Continued)

*Primary Examiner* — Jessica Weiss
(74) *Attorney, Agent, or Firm* — IP&T GROUP LLP

(57) ABSTRACT

A surgical implant and a surgical kit. The surgical implant has a body portion comprising a first hole formed in an exterior surface of the body portion, a second hole adjacent the first hole, and at least one through-hole within the body portion and extending entirely thought a depth of the body portion extending entirely thought a depth of the body portion. The implant has a central opening abutting the body portion and extending through the body portion. The first hole has a first sidewall and a first cavity in the body portion, the second hole has a second sidewall and a second cavity in the body portion, and the first cavity and the second cavity have an interconnected opening there between. The surgical kit includes the surgical implant and an intervertebral insertion device.

14 Claims, 27 Drawing Sheets

Related U.S. Application Data continuation-in-part of application No. 16/940,055, filed on Jul. 27, 2020.

(60) Provisional application No. 62/880,934, filed on Jul. 31, 2019.

(58) Field of Classification Search
USPC .......................................... 623/17.11–17.16
See application file for complete search history.

(56) References Cited

U.S. PATENT DOCUMENTS

| | | |
|---|---|---|
| 6,371,986 B1 | 4/2002 | Bagby |
| 6,371,987 B1 | 4/2002 | Weiland et al. |
| 6,503,279 B1 | 1/2003 | Webb et al. |
| 6,565,606 B1 | 5/2003 | Bruce et al. |
| 6,638,310 B2 | 10/2003 | Lin et al. |
| 6,673,075 B2 | 1/2004 | Santilli |
| 6,889,734 B2 | 5/2005 | Deger et al. |
| 6,911,249 B2 | 6/2005 | Wagner et al. |
| 7,056,577 B1 | 6/2006 | Bruce et al. |
| 7,255,713 B2 | 8/2007 | Malek |
| 7,553,539 B2 | 6/2009 | Bruce et al. |
| 7,662,186 B2 | 2/2010 | Bagga et al. |
| 7,918,891 B1* | 4/2011 | Curran .................... A61F 2/442 623/17.16 |
| 8,403,959 B2 | 3/2013 | Dollinger |
| 8,403,991 B2 | 3/2013 | Ullrich, Jr. et al. |
| 8,414,651 B2 | 4/2013 | Tyber et al. |
| 8,435,302 B2 | 5/2013 | Ulrich, Jr. et al. |
| 8,480,749 B2 | 7/2013 | Ullrich, Jr. et al. |
| 8,496,710 B2 | 7/2013 | Bagga et al. |
| 8,545,568 B2 | 10/2013 | Ulrich, Jr. et al. |
| 8,551,176 B2 | 10/2013 | Ullrich, Jr. et al. |
| 8,562,684 B2 | 10/2013 | Ullrich, Jr. et al. |
| 8,562,685 B2 | 10/2013 | Ullrich, Jr. et al. |
| 8,585,765 B2 | 11/2013 | Ullrich, Jr. et al. |
| 8,585,766 B2 | 11/2013 | Ullrich, Jr. et al. |
| 8,585,767 B2 | 11/2013 | Ullrich, Jr. et al. |
| 8,591,590 B2 | 11/2013 | Ullrich, Jr. et al. |
| 8,617,248 B2 | 12/2013 | Ullrich, Jr. et al. |
| 8,758,442 B2 | 6/2014 | Ullrich, Jr. et al. |
| 8,758,443 B2 | 6/2014 | Ullrich, Jr. et al. |
| 8,814,939 B2 | 8/2014 | Ullrich, Jr. et al. |
| 8,834,571 B2 | 9/2014 | Bagga et al. |
| 8,940,053 B2 | 1/2015 | Ulrich, Jr. et al. |
| 8,992,619 B2 | 3/2015 | Patterson et al. |
| 8,992,622 B2 | 3/2015 | Ullrich, Jr. et al. |
| 9,011,546 B2 | 4/2015 | Ullrich, Jr. et al. |
| 9,125,756 B2 | 9/2015 | Ullrich, Jr. et al. |
| 9,168,147 B2 | 10/2015 | Patterson et al. |
| 9,226,992 B2 | 1/2016 | Mann et al. |
| 9,314,337 B2 | 4/2016 | Patterson et al. |
| 9,327,051 B2 | 5/2016 | Ullrich, Jr. et al. |
| 9,421,053 B2 | 8/2016 | Kennedy et al. |
| 9,433,511 B2 | 9/2016 | Bagga et al. |
| 9,498,349 B2 | 11/2016 | Patterson et al. |
| 9,610,174 B2 | 4/2017 | Wang et al. |
| 9,615,935 B2 | 4/2017 | Patterson et al. |
| 9,642,721 B2 | 5/2017 | Patterson et al. |
| 9,649,200 B2* | 5/2017 | Wickham ............ A61F 2/30767 |
| 9,655,745 B2 | 5/2017 | Patterson et al. |
| 9,700,431 B2 | 7/2017 | Nebosky et al. |
| 9,724,205 B2 | 8/2017 | Lin et al. |
| 9,848,995 B2 | 12/2017 | Ullrich, Jr. et al. |
| 9,987,051 B2 | 6/2018 | Nunley et al. |
| 10,064,741 B2 | 9/2018 | Kennedy et al. |
| 10,111,753 B2 | 10/2018 | Patterson et al. |
| 11,547,576 B2* | 1/2023 | Ahn ...................... A61F 2/4455 |
| 2003/0055505 A1 | 3/2003 | Sicotte et al. |
| 2004/0158327 A1 | 8/2004 | Bagby |
| 2006/0116766 A1 | 6/2006 | Lemaire |
| 2006/0173542 A1 | 8/2006 | Shikinami |
| 2008/0077248 A1 | 3/2008 | Murillo et al. |
| 2008/0154379 A1 | 6/2008 | Steiner et al. |
| 2009/0012620 A1 | 1/2009 | Youssef et al. |
| 2009/0187245 A1 | 7/2009 | Steiner et al. |
| 2010/0228296 A1* | 9/2010 | Vraney .................. A61F 2/447 606/279 |
| 2010/0268339 A1* | 10/2010 | Malinin .................. A61F 2/447 623/17.11 |
| 2011/0082551 A1* | 4/2011 | Kraus .................... A61F 2/3603 623/17.11 |
| 2011/0301709 A1* | 12/2011 | Kraus .................... A61F 2/4465 623/17.11 |
| 2012/0083882 A1 | 4/2012 | Shih et al. |
| 2013/0006363 A1* | 1/2013 | Ullrich, Jr. ............ A61F 2/3094 623/17.16 |
| 2013/0116793 A1* | 5/2013 | Kloss ..................... A61F 2/442 623/17.16 |
| 2014/0142708 A1 | 5/2014 | Peterman et al. |
| 2016/0022431 A1* | 1/2016 | Wickham ................ A61F 2/447 623/17.16 |
| 2016/0213485 A1* | 7/2016 | Schaufler ............ A61B 17/7059 |
| 2016/0213486 A1* | 7/2016 | Nunley ................ A61F 2/4455 |
| 2016/0213487 A1* | 7/2016 | Wilson ................ A61F 2/4465 |
| 2016/0213488 A1* | 7/2016 | Moore .................. A61F 2/4465 |
| 2016/0228604 A1 | 8/2016 | Mann et al. |
| 2017/0216036 A1* | 8/2017 | Cordaro .................... A61F 2/44 |
| 2017/0312089 A1* | 11/2017 | Duarte ................ A61F 2/30771 |
| 2018/0296343 A1 | 10/2018 | Wei |
| 2018/0368991 A1 | 12/2018 | Levieux |
| 2019/0054536 A1 | 2/2019 | Xu et al. |
| 2019/0076258 A1* | 3/2019 | Black ..................... B33Y 80/00 |
| 2019/0091027 A1* | 3/2019 | Asaad ..................... A61F 2/447 |
| 2019/0142600 A1* | 5/2019 | Tipping ................. A61L 27/50 623/17.11 |
| 2019/0343644 A1* | 11/2019 | Ryan ................... A61F 2/30771 |
| 2019/0343650 A1* | 11/2019 | Petersheim ............ A61F 2/442 |
| 2020/0046512 A1 | 2/2020 | Newman et al. |

OTHER PUBLICATIONS

Notice of Allowance for the U.S. Appl. No. 17/132,177 issued by the USPTO dated Mar. 31, 2021.

Office Action for the U.S. Appl. No. 16/940,055 issued by the USPTO dated Oct. 20, 2022.

Notice of Allowance for the U.S. Appl. No. 16/940,055 issued by the USPTO dated Feb. 7, 2023.

\* cited by examiner

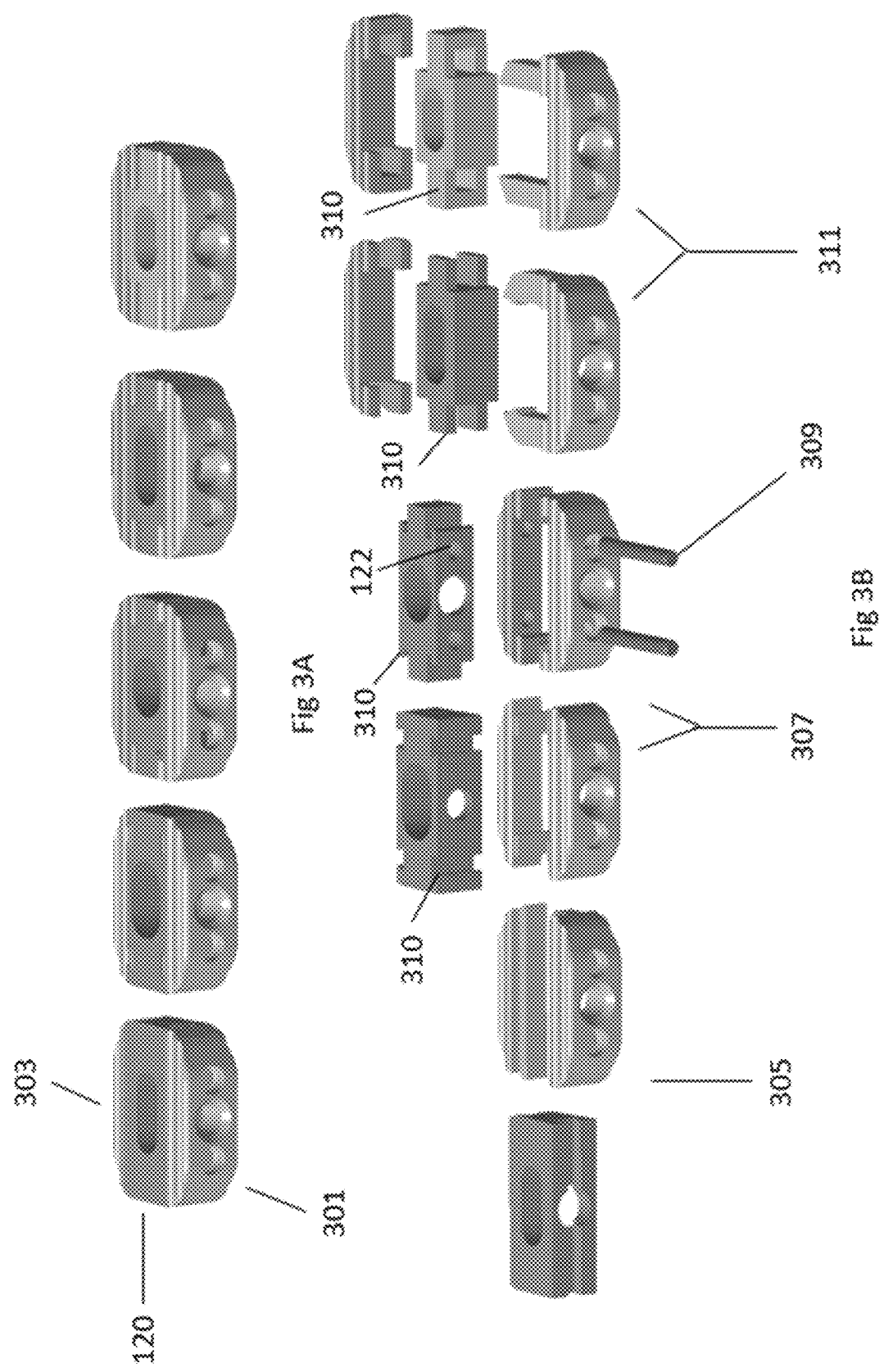

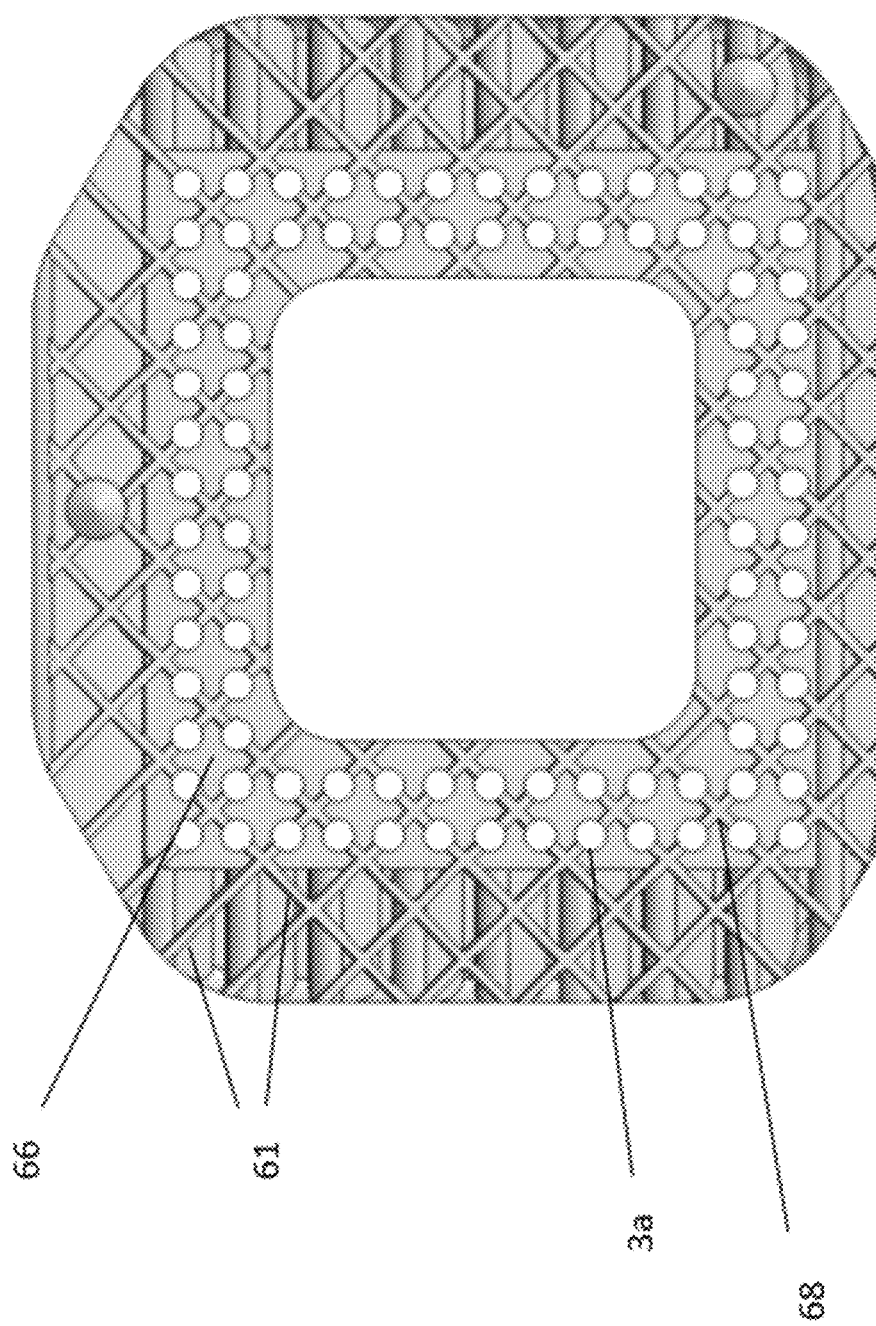

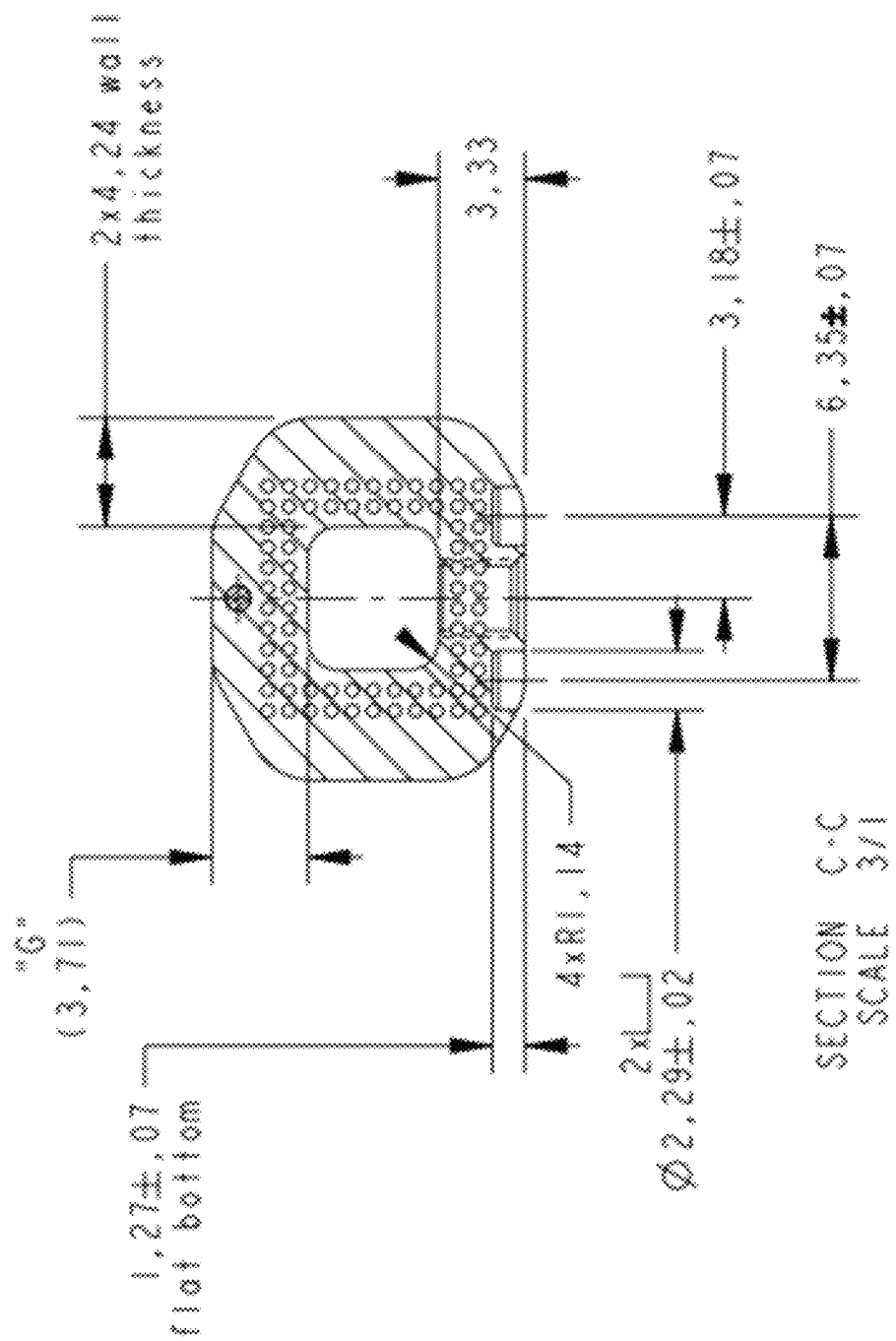

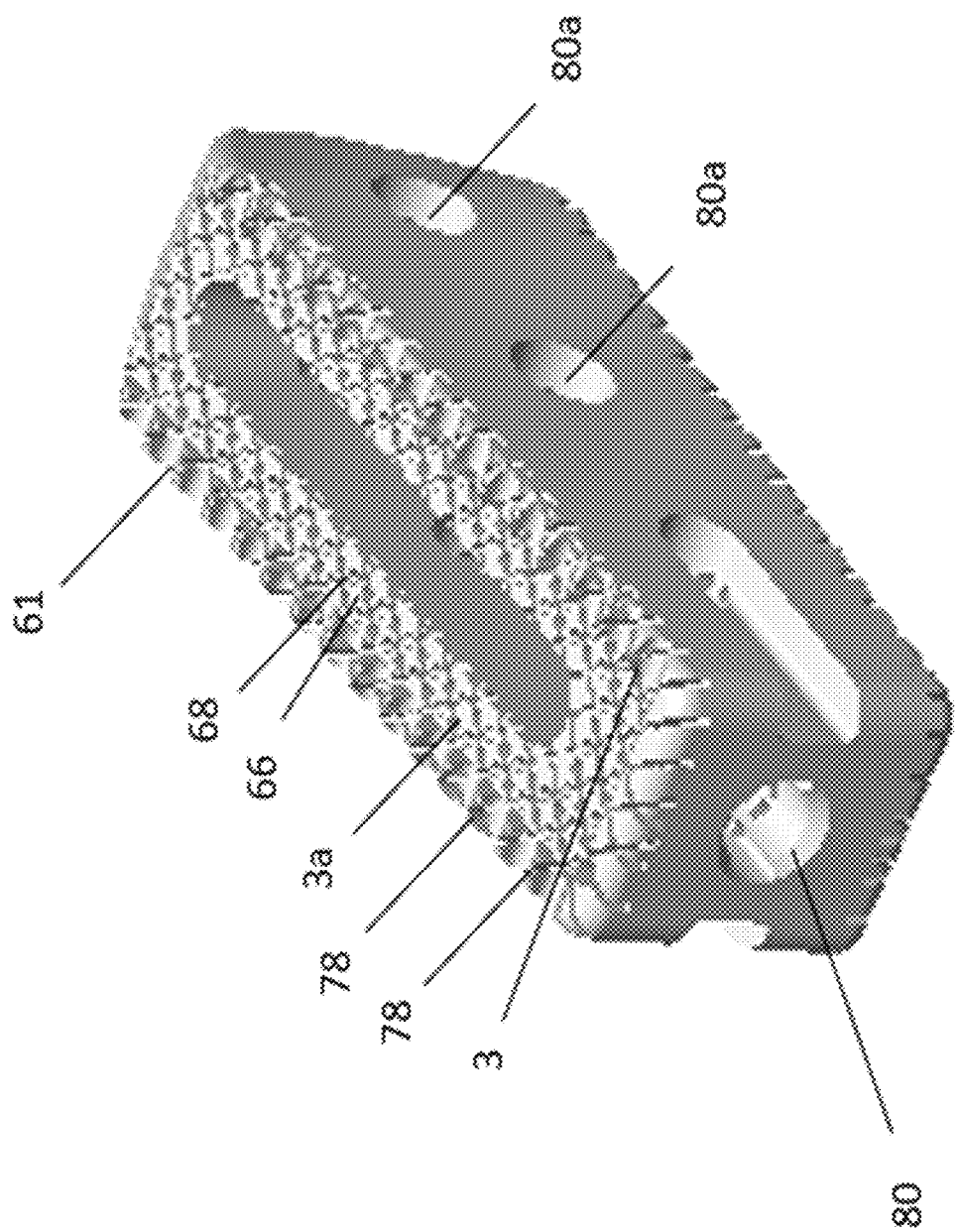

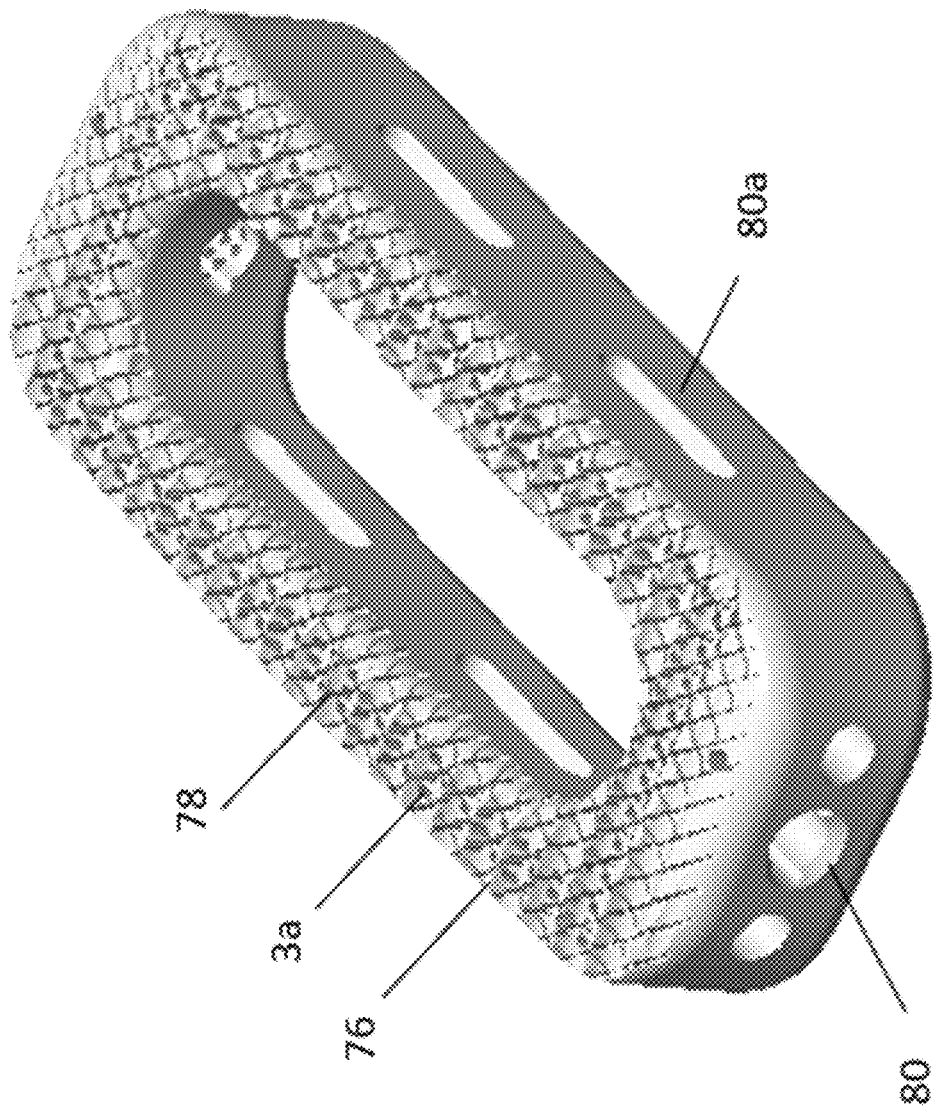

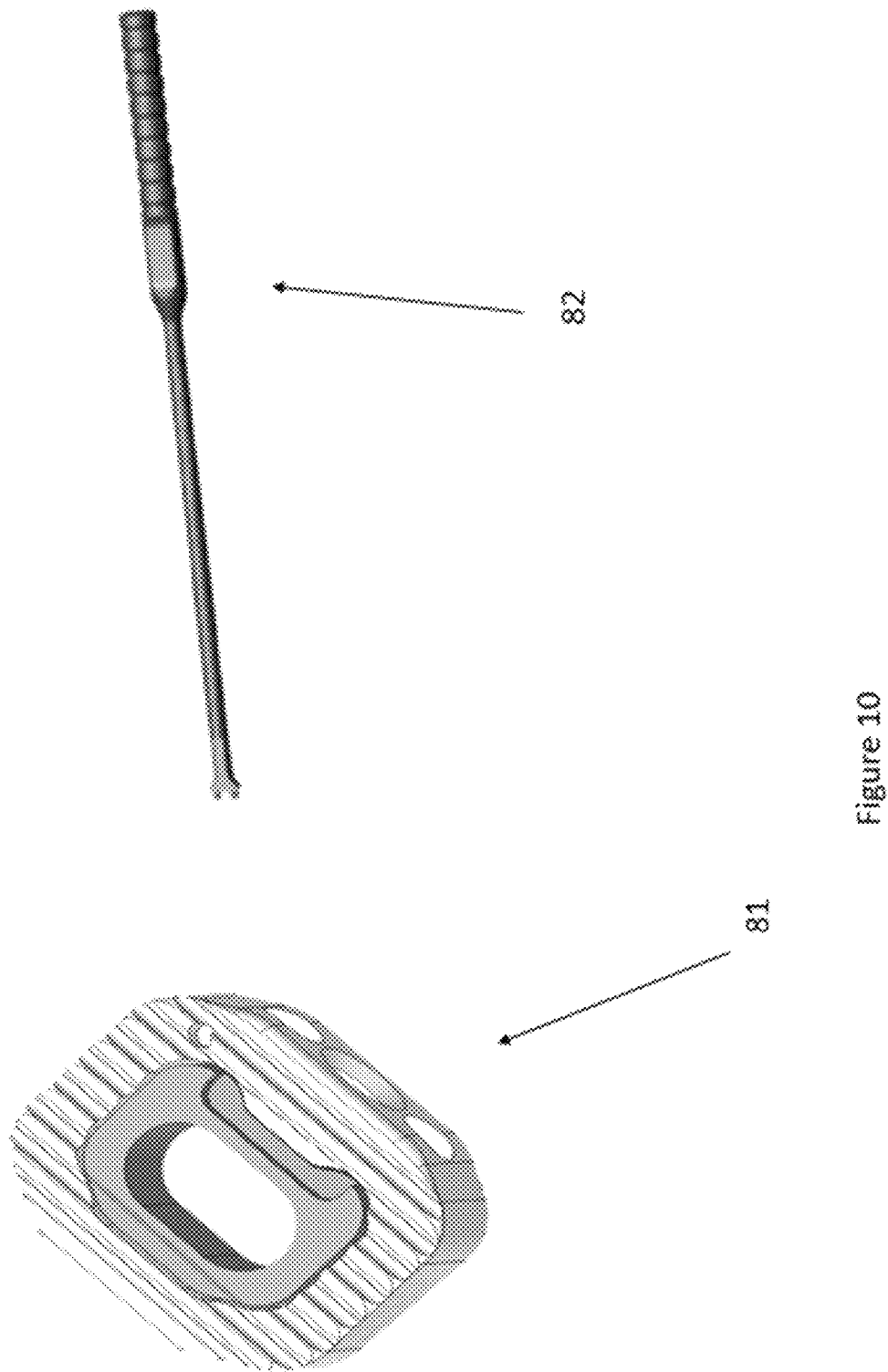

POROUS SPINAL IMPLANT

CROSS REFERENCE TO RELATED APPLICATIONS

This application is a continuation of U.S. Ser. No. 17/132,177 filed Dec. 23, 2020 entitled "POROUS SPINAL IMPLANT" (the entire contents of which are incorporated herein by reference) which is continuation in part of U.S. Ser. No. 16/940,055 filed Jul. 27, 2020 entitled "POROUS SPINAL IMPLANT" (the entire contents of which are incorporated herein by reference) which is related to and claims priority to U.S. Ser. No 62/880,934 filed Jul. 31, 2019 and entitled "POROUS SPINAL IMPLANT," the entire contents of which are incorporated herein by reference.

BACKGROUND OF THE INVENTION

Field of the Invention

The present invention relates to implant devices for treating in particular spinal disorders.

Description of the Related Art

Disorders of the spine often result in degeneration of the spinal disc in the intervertebral space between the vertebral bodies. Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-operative treatment requires patients to adjust their lifestyles and submit to pain relievers and a level of underlying pain. Operative treatment options include disc removal or insertion of devices or bone grafts to fixate or fuse vertebra together. Screw and rod systems, interbody spacers, threaded fusion cages, and the like could be used.

In the case of disc removal, the previously disc separated vertebral bodies can collapse or misalign. This can cause spinal instability, abnormal joint mechanics, arthritis, nerve damage, and severe pain. To prevent this, the removed disc is usually replaced with prosthetic spacers constructed from a biocompatible synthetic material or allograft bone. These spacers can become dislodged leading to severe complications. Pathways that permit or stimulate bone growth and allow adjacent vertebra to fuse together can help prevent this. Such bone growth helps ensure adequate implant retention and helps strengthen the vertebral joint. Moreover, mimicking the bone density of adjacent vertebra can help prevent implant rejection and non-union.

All contents of the following patent documents are incorporated herein by reference and provide information as to the state of the art prior to this invention:

1. U.S. Pat. No. 6,565,606, Implant, method of making the same and use the same;
2. U.S. Pat. No. 9,987,051, Interbody spacer;
3. US 2009/0012620A1, Implantable Cervical Fusion Device;
4. US 2014/0142708, Spinal system and method including lateral approach;
5. US 2016/0213485, Interbody spacer;
6. U.S. Pat. No. 5,904,719, Interbody fusion device having partial circular section cross-sectional segments;
7. U.S. Pat. No. 6,371,986, Spinal fusion device, bone joining implant, and vertebral fusion implant;
8. U.S. Pat. No. 6,371,987, Device for connecting vertebrae of the vertebral column;
9. U.S. Pat. No. 6,503,279, Intervertebral implant;
10. U.S. Pat. No. 6,638,310, Intervertebral spacer and implant insertion instrumentation;
11. U.S. Pat. No. 6,673,075, Porous intervertebral spacer;
12. U.S. Pat. No. 6,889,734, Tire chain;
13. U.S. Pat. No. 7,056,577, Body for providing ingrowth and growth of bone tissue and/or connective tissue and method of making such a body;
14. U.S. Pat. No. 7,225,713, Cutting blade for a motor-driven, manually-guided implement;
15. U.S. Pat. No. 9,226,992, Implantable cartilaginous tissue repair device;
16. U.S. Pat. No. 8,814,939, Implants having three distinct surfaces;
17. U.S. Pat. No. 9,327,051, Implants with integration surfaces having regular repeating surface patterns;
18. U.S. Pat. No. 9,610,174, Intervertebral implant;
19. U.S. Pat. No. 9,700,431, Orthopaedic implant with porous structure member;
20. U.S. Pat. No. 7,553,539, Grain for providing cell growth;
21. U.S. Pat. No. 8,414,651, Dynamic interbody;
22. U.S. Pat. No. 9,314,337, Microstructured implant surfaces;
23. U.S. Pat. No. 9,724,205, Biodegradable implant for intertransverse process fusion;
24. U.S. Pat. No. 9,433,511, Interbody spinal implant having a roughened surface topography;
25. US 2003/0055505, Intervertebral fusion device;
26. US 2004/0158327, Bone joining implant with retaining tabs;
27. US 2006/0173542, Biomaterial for artificial cartilage;
28. US 2006/0116766, Anterior lumbar interbody implant;
29. US 2008/0077248, Vertebral body replacement;
30. US 2008/0154379, Interbody fusion hybrid graft;
31. US 2009/0187245, Interbody fusion hybrid graft;
31. US 2012/0083882, Spinal implant structure and method for manufacturing the same;
32. US 2016/0228604, Method for the manufacture of an implantable cartilaginous tissue repair device; and
33. US 2017/0312089, Bone growth enhancing implant.

SUMMARY OF THE INVENTION

In one embodiment, there is provided a surgical implant comprising: a body having at least one interior surface, the body forming a peripheral support for the implant; a porous insert comprised of a porous material, having at least one axially-extending hole, and attached to the body along the at least one interior surface such that the porous material extends across a height of the body; and the porous insert comprising a locking mechanism formed in the porous insert or extending from the porous insert, the locking mechanism minimizing movement of the porous insert within the body.

In one embodiment, there is provided a surgical implant. The surgical implant has a body portion comprising a first hole formed in an exterior surface of the body portion, a second hole adjacent the first hole, and at least one through-hole within the body portion and extending entirely thought a depth of the body portion extending entirely thought a depth of the body portion. The implant has a central opening abutting the body portion and extending through the body portion. The first hole has a first sidewall and a first cavity in the body portion, the second hole has a second sidewall and a second cavity in the body portion, and the first cavity and the second cavity have an interconnected opening there between.

In one embodiment, there is provided a kit comprising the surgical implant described above and an intervertebral insertion device.

In one embodiment, there is provided a method for securing two bones surfaces together. The method comprises providing between the two bone surfaces the surgical implant described above; supplying bone graft into a porous insert of the surgical implant; and securing the porous surface with the bone graft material in place between the two bone surfaces.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

FIG. 3A is a perspective view of another embodiment of the implant device;

FIG. 3B shows a method of assembling the embodiment shown in FIG. 3A;

FIG. 9C is a top view of the implant device of FIG. 9B;

FIG. 9F is a scaled drawing of the implant device of FIG. 9B;

FIG. 9H is a perspective view of yet another implant device of the invention;

FIG. 9J is a perspective view of still another implant device of the invention;

FIG. 10 is a view of a kit according to one embodiment of the invention with the kit including an implant device and an inserter tool;

DETAILED DESCRIPTION OF THE INVENTION

The implants in one embodiment of this invention are designed for spinal fusion procedures.

Surgical spacers exist in the art. U.S. Pat. No. 5,702,449, which is hereby incorporated by reference in its entirety, teaches an implant with a body and a sleeve where the sleeve is composed of material that is stronger under compressive loads than the body. U.S. Pat. Appl. Publ. No. 2009/0012620 A1, which is hereby incorporated by reference in its entirety, teaches an implantable intervertebral device made of bone with a cavity extending throughout the body that is filled with osteoconductive or osteoinductive graft material. U.S. Pat. Appl. Publ. No. 2014/0142708A, which is hereby incorporated by reference in its entirety, teaches a surgical implant designed to conform to the adjacent endplates such that cutting and manipulation of bone is minimized. Several methods to promote bone growth have also been tried. U.S. Pat. No. 9,987,051 B2, which is hereby incorporated by reference in its entirety, teaches a surgical implant with a cavity that increases in width at a medial position and includes a plurality of orifices. U.S. Pat. Nos. 6,123,705 and 6,447,547, each of which are hereby incorporated by reference, teach perforated implants. Although these patents describe implants and methods for promoting bone growth and healing, it remains a slow process which does not always end up in the successful securing of one bone surface to another.

Figure 1A:
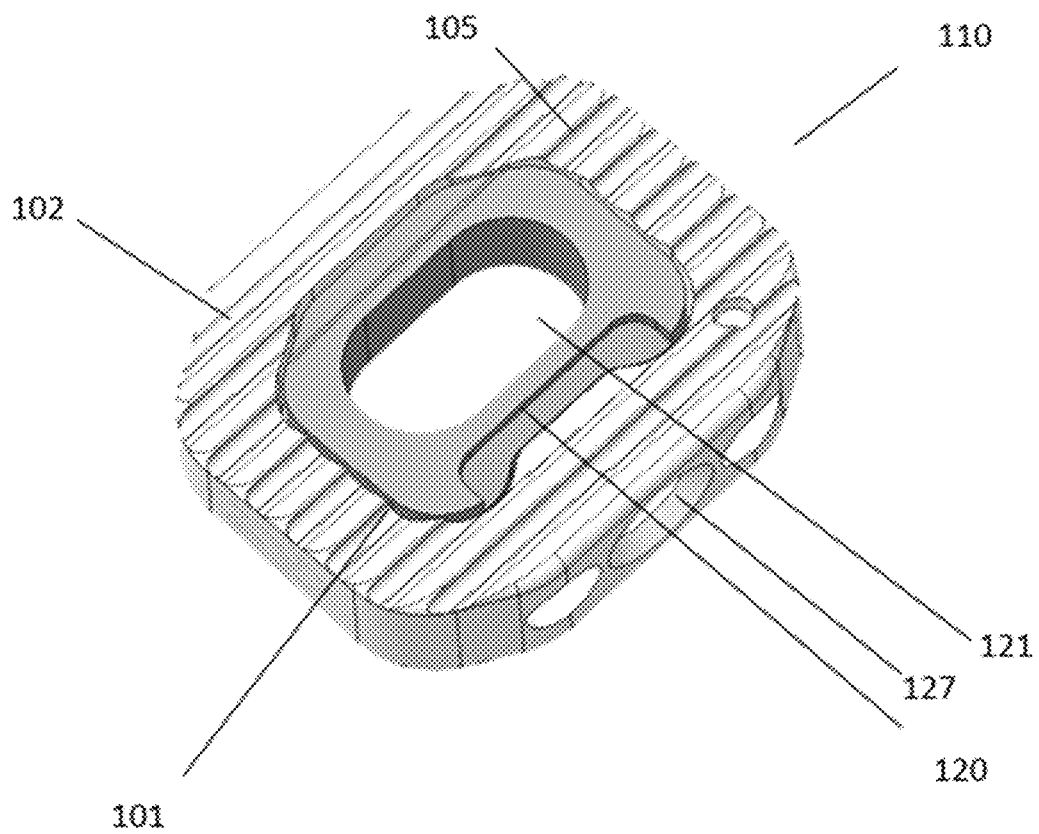
FIG. 1A is a perspective view of one embodiment of the implant device.

In one embodiment of the invention, there is provided as shown in FIG. 1A a surgical implant 110 comprising a body 105 having a peripheral section 102 and at least one central opening 101 extending into the body 105, and at least one porous insert 120 inserted into the central opening(s) 101, with the porous insert 120 having its own vertical (or axially extending) opening(s) 121. Threaded opening 127 extends through the front face of the peripheral section 102 and allow the attachment of an insertion device. The peripheral section 102 can serve as the primary load bearing member.

In one embodiment of the invention, the body 105 has at least one interior surface 106, and the porous insert 120 is comprised of a porous material, and has therein an axially-extending opening 121. The porous insert 120 is attached to the body 105 along the at least one interior surface 106 such that the porous material extends across a height of the body, and preferably does not extend beyond an uppermost surface of body 105.

In one embodiment of the invention, the porous insert 120 has a locking mechanism formed therein or extending therefrom which is configured to prevent the porous insert 120 from moving within the body. In one embodiment of the invention, the porous insert 120 has a plurality of interconnected holes extending throughout a section of the porous insert. The interconnected holes are of a predefined size. See for example holes 3 in FIG. 5A which can be applied to the porous insert 120.

In one embodiment of the invention, the interconnected holes extend linearly across a section of the porous insert. In one embodiment of the invention, the interconnected holes extend linearly and diagonally across a section of the porous insert. In one embodiment of the invention, the interconnected holes are of a predefined size. For example, the interconnected holes can have a width or diameter between 100 to 1000 microns, 200 to 800 microns, 250 to 700 microns, and/or 300 to 600 microns (or any intervening ranges or values in between). These sizes of the interconnected holes may (after insertion into a patient and if conditions are favorable) promote bone growth in the porous insert 120. As used herein, predefined means that the holes are created or the porous implant is selected such that the holes are of a standard or nominal (average)size typically, but not necessarily, formed by an engineering process making the holes by lithography, etching, machining, or printing (three-dimensional printing) determined by the characteristics of the engineering process. The porosity of the porous insert 120 ranges from 20 to 70%, or from 30 to 50%, or from 40 to 45%, and includes intermediate and overlapping ranges of these porosities.

Figure 1B:
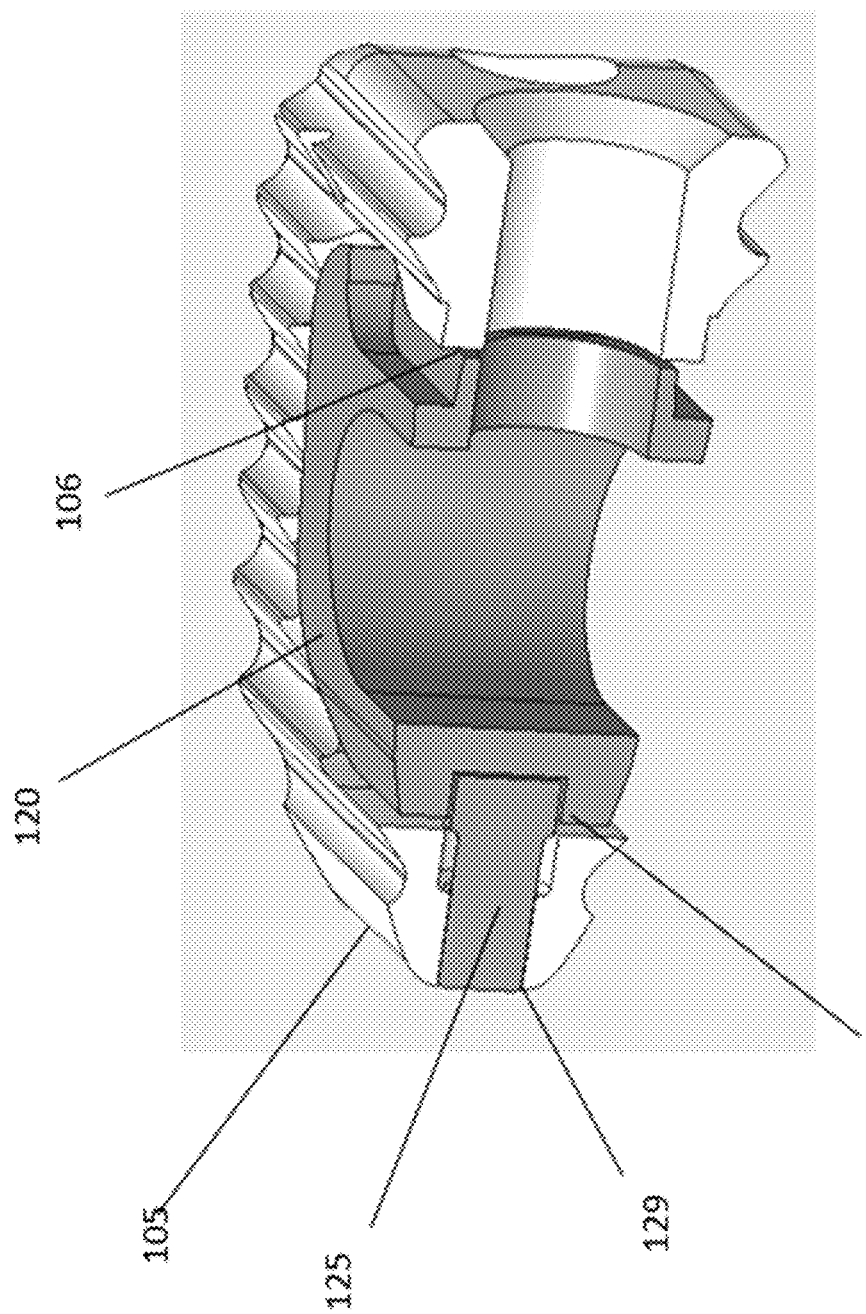
FIG. 1B is a sectional view of one embodiment of the implant device.
Figure 1C:
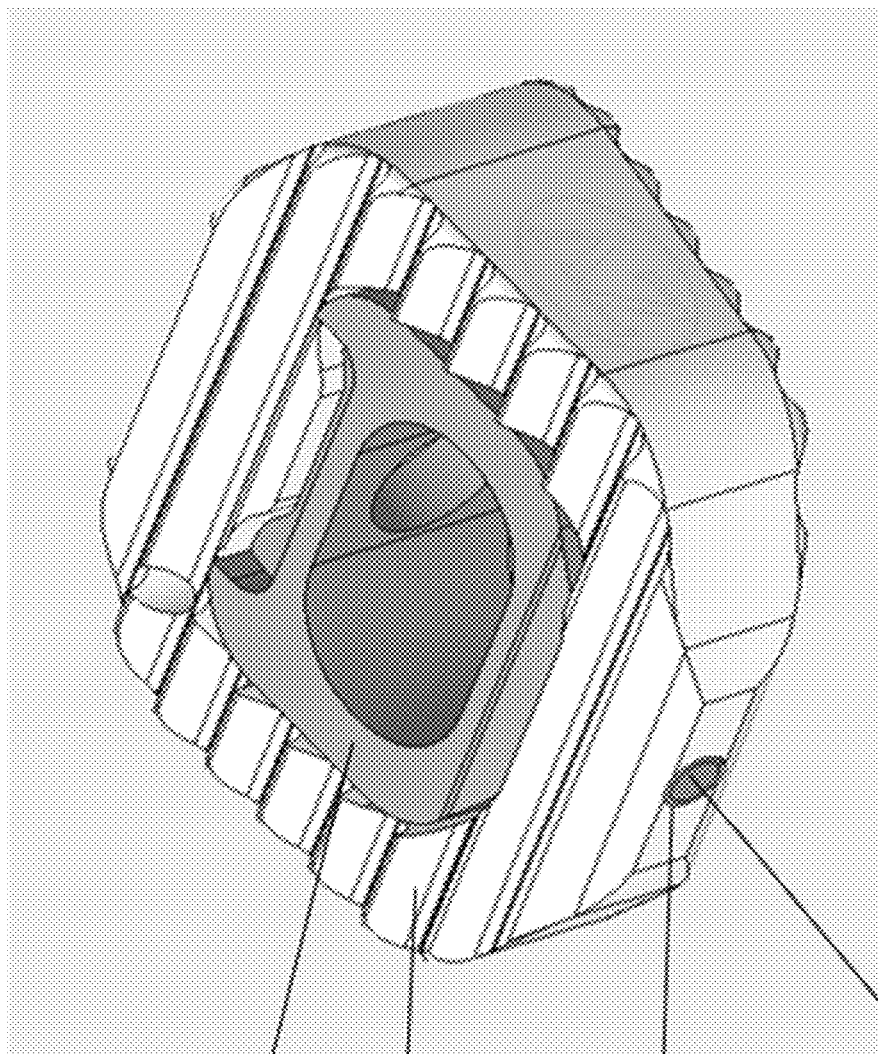
FIG. 1C is another perspective view of one embodiment of the implant device.

Body 105 may be formed of various metals such as for example cobalt chrome, stainless steel or titanium including its alloys, various plastics including those which are bioabsorbable, and various ceramics or combinations of these materials. In one embodiment, body portion 105 is made of medical grade PEEK (Polyetheretherketone may comprise 5% to 75% carbon fibers by weight percent. In one embodiment the insert 120 has locking mechanisms 123 and 125, at least one of which has shown is formed in the insert 120. In this embodiment, recess 123 formed in the insert 120 is configured to receive locking pin 125 which extends through hoke 129 in body portion 105, as shown in the sectional and perspective view of FIGS. 1B and 1C. This locking mechanism prevents insert 120 from moving once it is disposed in the body 105. Insert 120, as would be understood by one with skill in the art, is not limited by shape. Insert 120 could have any regular geometrical shape (square, rectangular, circular) or any irregular shape without leaving the contemplated nature of the invention.

In an embodiment the body 105 is tapered such that the body 105 has a distal end with a smaller height than a proximal end. In an embodiment the body 105 is composed of peak or modified peak. The peak composing body 105 may comprise 5% to 75% carbon fibers by weight percent. Body 105 may have at least one rounded edge. This rounded edge may extend laterally along either the posterior or anterior side of body 105. Body 105 may or may not be grooved as shown in FIG. 1A. In an embodiment insert 120 is composed of porous titanium. Although described with here with respect to pure titanium, titanium alloys such as titanium-6 aluminium-4 vanadium or other metals such as zirconium may be used.

In another embodiment, insert 120 is composed of porous titanium but with an outer layer of titanium dioxide. The outer layer of titanium dioxide could be formed by exposing insert 120 to air or artificially produced by exposing insert body 120 to high temperatures, an oxidizing gas, strong oxidants in a wet chemical environment, or through an electrochemical process such as anodic oxidation.

Figure 1D:
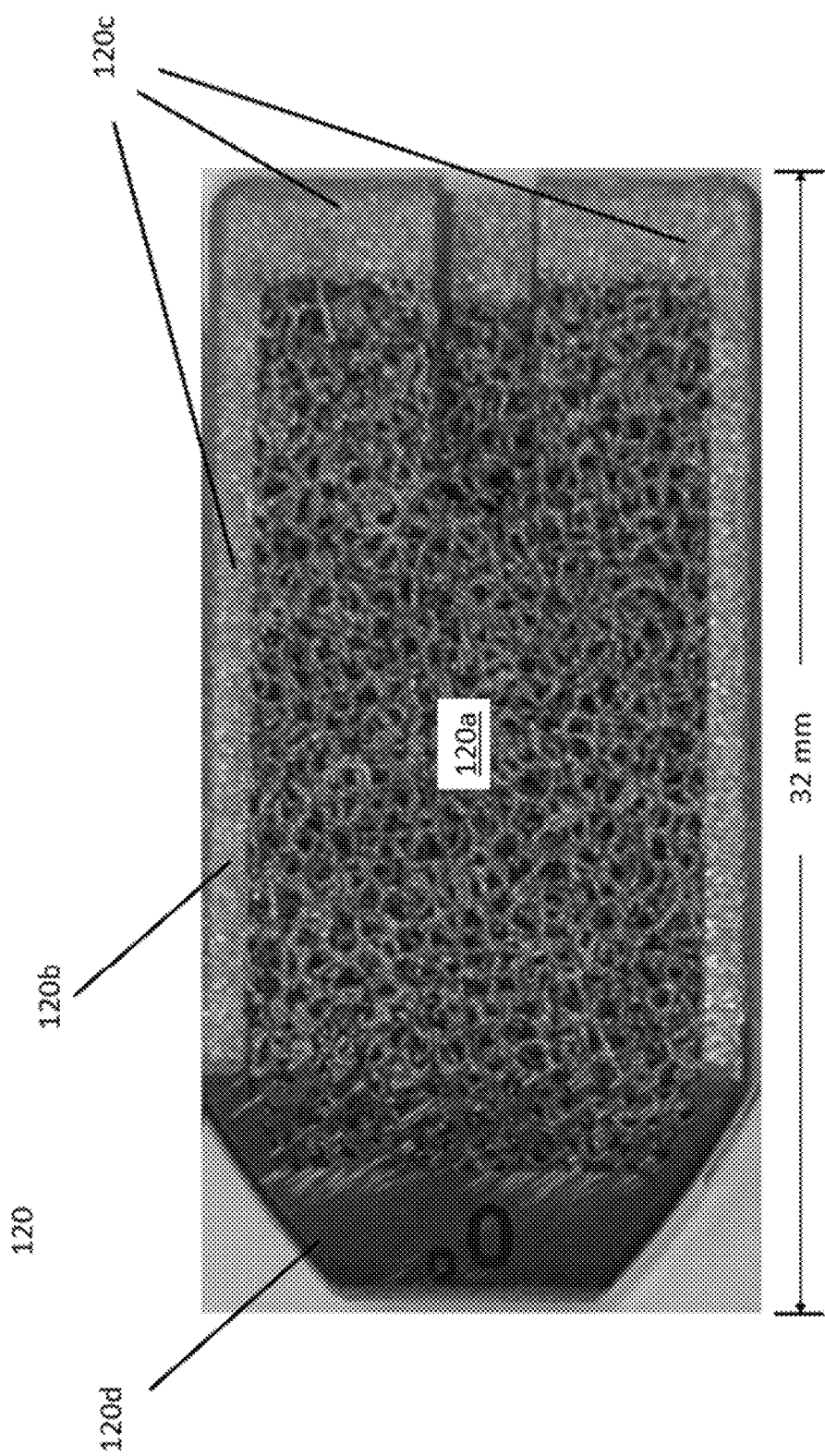
FIG. 1D is a scaled photographic depiction of a porous surface of a three-dimensionally printed porous insert.

In another embodiment, insert 120 is 3-D printed through laser sintering or any process known in the art. FIG. 1D is a photographic depiction of a porous surface 120a of a three-dimensionally printed porous insert 120. In this example, an edge section 120b of the porous insert 120 forming a part of a frame 120c on the perimeter can have a different porosity that an interior section 120c of porous insert 120. In this example, an edge section 120b of the porous insert 120 has a lower porosity than the interior section 102c. and may be a solid material. As depicted, insert 102 may have a tapered section 120d made of a solid material, with the tapering facilitating insertion between vertebrae.

Accordingly, in one embodiment, the implants 110 of the present invention can be composed entirely of metal with for example a solid metal frame (acting as peripheral section 102 for supporting the weight of the spinal column) and one or more porous sections for promotion of bone growth once the insert is implanted. Meanwhile, in one embodiment, the three dimensionally printed inserts 120 may be a part of implant 110 shown in FIG. 1A, with the implant 110 having a body 105 and a peripheral section 102 forming a place where the porous insert 120 can be disposed.

As examples of suitable ways to make porous insert 120 or other porous bodies of the invention, the techniques described in US 20190054536 (the entire contents of which are hereby incorporated in its entirety) can be used to make the porous bodies of this invention. Alternatively, the techniques described in US 20180296343 (the entire contents of which are hereby incorporated in its entirety) can be used to make the porous bodies of this invention. Insert 120 could also be formed through gel or other foaming techniques, molding, use of the Hunter or Kroll process, or any other method known in the art as described in US 2012/0310357 (the entire contents of which are hereby incorporated in its entirety).

In one embodiment, insert 120 has pore sizes on the exposed surfaces on the order of approximately 400-600 μm. In other embodiments, the pore size may be between 100 to 1000 microns, 200 to 800 microns, 250 to 700 microns, 300 to 600 microns, about 0.1 mm to about 5 mm, about 0.5 mm to about 3 mm, or about 1 mm to about 2 mm (or any intervening ranges or values in between). Insert 120 could contain continuous pores, non-continuous pores, or a mixture of both.

Figure 2A:
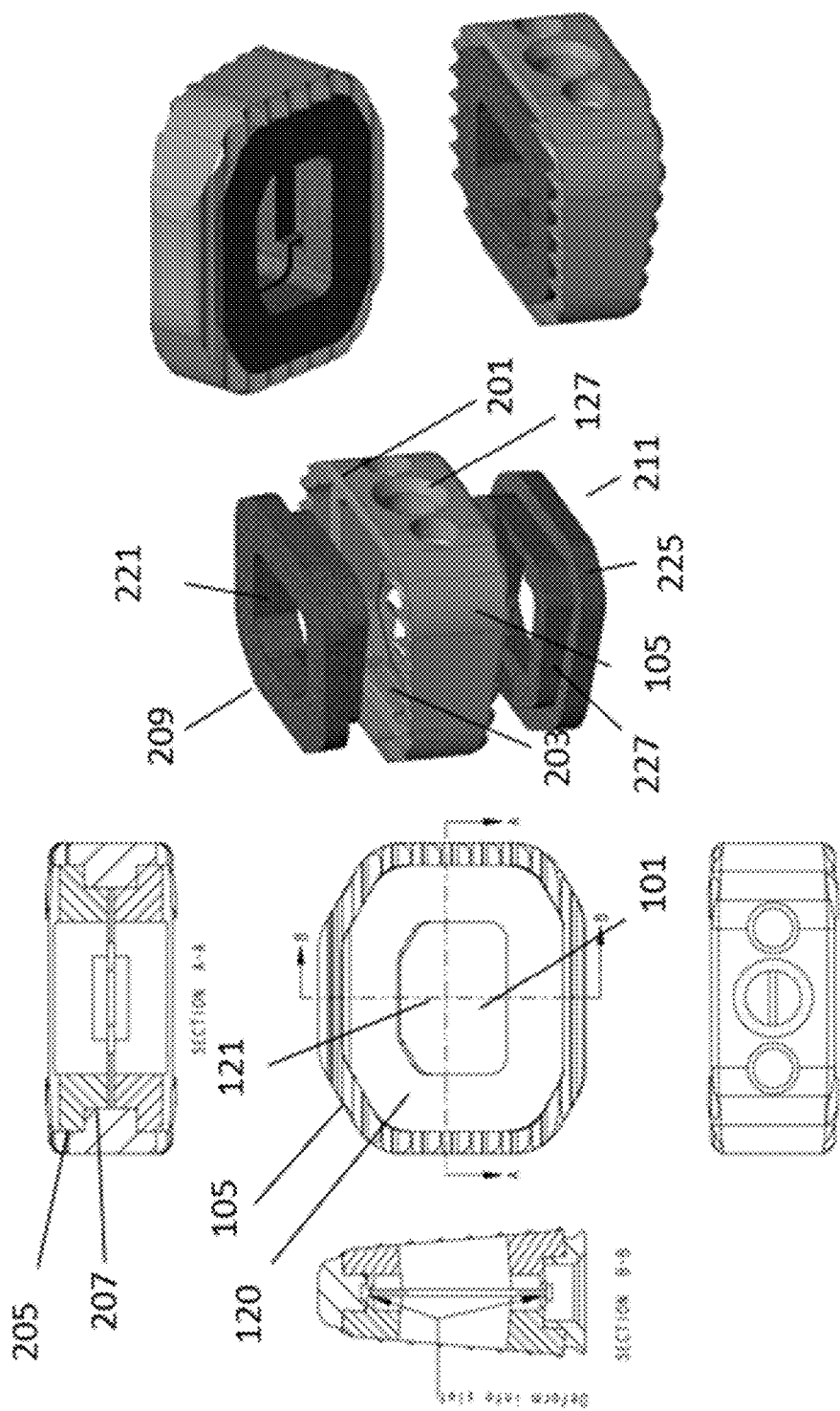
FIG. 2A is a perspective view of another embodiment of the implant device.

FIG. 2A shows a perspective view of one embodiment of the device 10. In this embodiment, aperture 101 extends through a body 105 which may comprise a rounded edge 201 and teeth 203 along a surface of body 105. In FIG. 2A, aperture 101 has a first perimeter sidewall 205 and a second perimeter sidewall 207 of smaller diameter than and positioned underneath the first perimeter sidewall 205. This embodiment may also include an upper insert 209 and lower insert 211 composed of a different or similar material than body 105. Inserts 209 and 211 may each have a through hole 221 aligned with the aperture of the body 105.

At least one of the inserts 209 and 211 may have a flange 225 (i.e., an extrusion) which contacts a lateral surface adjoining the first perimeter sidewall to the second perimeter sidewall. The size of the flange 225 of the porous body may be slightly oversized with respect to the interior size formed first perimeter sidewall 205. Similarly, the size of the vertical extrusion 227 of the porous body may be slightly oversized with respect to the interior size formed by second perimeter sidewall 207. By having any of these extrusions oversized, the porous body once inserted is fixed inside the implant. Inserts 209 and 211 may or may not contact each other at the center of body 105. Insert 209 may be disposed downward in the aperture and insert 211 may be disposed upward.

Figure 2B:
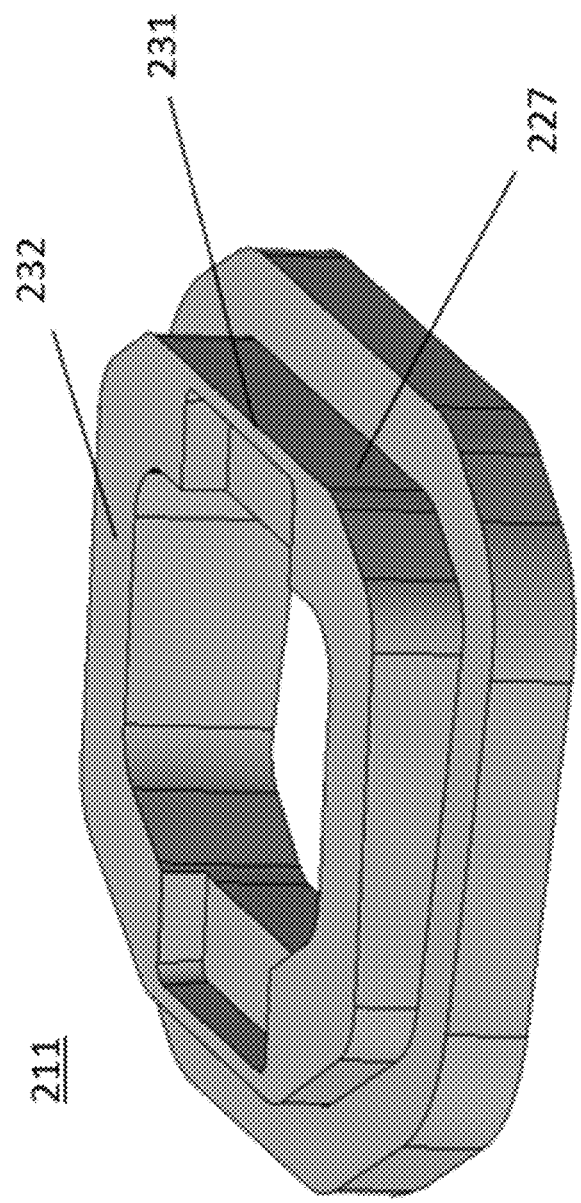
FIG. 2B is a perspective view of one of the porous inserts of the implant device of FIG. 2A.
Figure 2C:
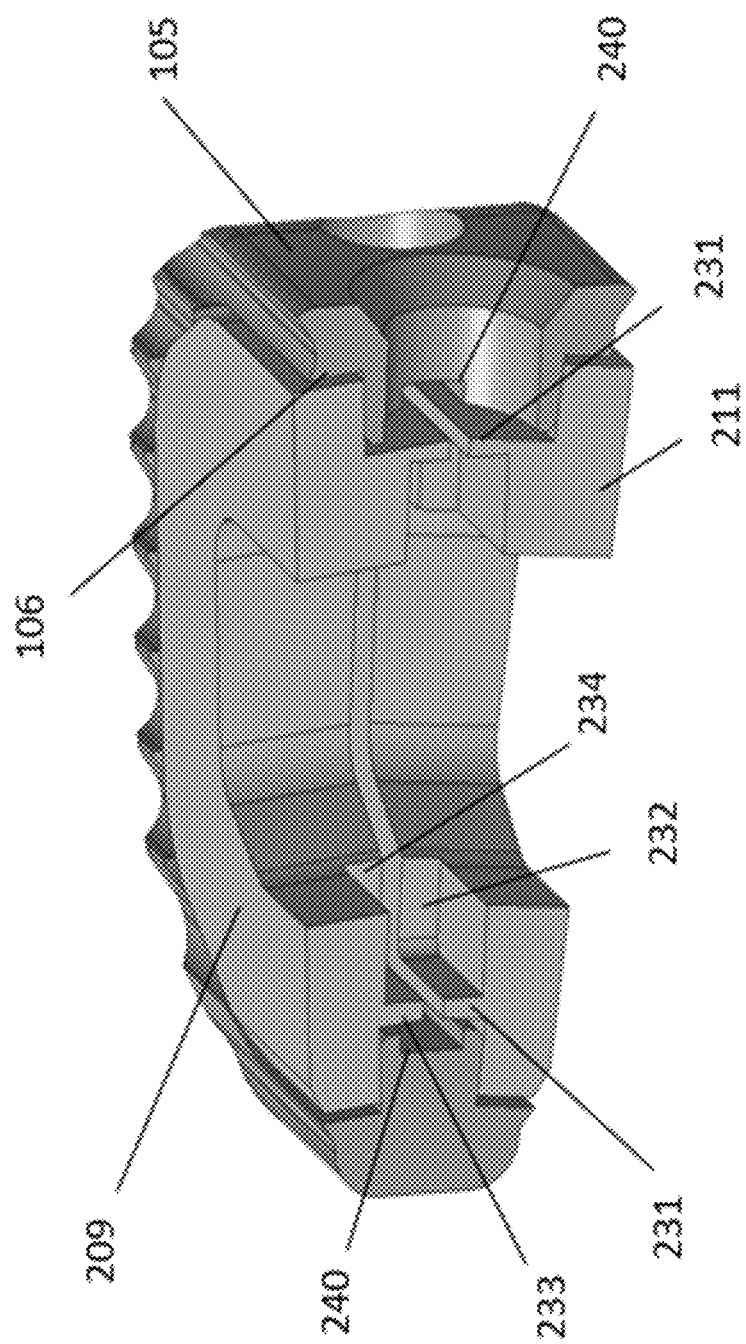
FIG. 2C is a sectional view of both porous inserts of the implant device of FIG. 2A.

FIG. 2B is a perspective view of porous insert 211 of the implant device of FIG. 2A. In this embodiment, vertical extrusion 227 of the porous insert 211 is made with one section 231 having a thinner wall than an adjacent section 232. FIG. 2C is a sectional view of both halves of the porous insert of the implant device of FIG. 2A. (The upper insert 209 similarly has one section 233 having a thinner wall than an adjacent section 234.) Once the inserts 209 and 211 are in place as shown in FIG. 2C, a tool (not shown) can be used push the thinner wall sections 231 into recesses 240 in the body 105, and thereby providing a locking mechanism for this embodiment. While as shown, the thinner wall sections 231, 233 are themselves of the same porous material as the respective inserts 209 or 211, the thinner wall sections 231 can be made of a different porous material or a non-porous material.

For example, inserts 209 and 211 may be comprised of porous titanium or any of the same materials as insert body 120. Like insert body 120, inserts 209 and 211 could be 3-D printed, formed through gel or other foaming techniques, molding use of the Hunter or Kroll process, or any other method known in the art as described in US/2012/0310357 previously incorporated by reference. Inserts 209 and 211 can have the pore sizes noted above pores, and could contain continuous, non-continuous or a mixture of continuous and non-continuous pores. Threaded opening 127 extends through the front face of the peripheral section 102 and permits the attachment of an insertion device (not shown here).

As shown in FIG. 3A, body 105 may be composed of two complementary sections 301 and 303. In this embodiment, insert 120 may engage both complementary sections 301 and 303. Complementary sections 301 and 303 may be comprised maybe formed of the same materials as described above for body 105. The embodiment shown in FIG. 3A could be assembled as where insert body 120 may slide longitudinally 305 or vertically 307 into place between the two complementary sections 301 and 303. The complimentary sections can have a number of interlocking components (as described below) which form another locking mechanism of the present invention. Rods or pins 309 may also connect insert 120 to complementary sections 301 and 303. Through holes 122 in the porous insert 120 in one embodiment form another locking mechanism of the present invention. Alternatively, complementary sections 301 and 302 may horizontally sandwich 311 insert 120 and connect using a hook and eye system.

FIG. 3B shows a method of assembling the embodiment shown in FIG. 3A. As shown in FIG. 3B, locking extrusions 310 can slide around protrusions on the body portions 301, 303, as for example dovetail-type connectors. Also, locking extrusions 310 can fit into slots in the body portions 301, 303. Locking extrusions 310 in one embodiment form another locking mechanism of the present invention.

Figure 4B:
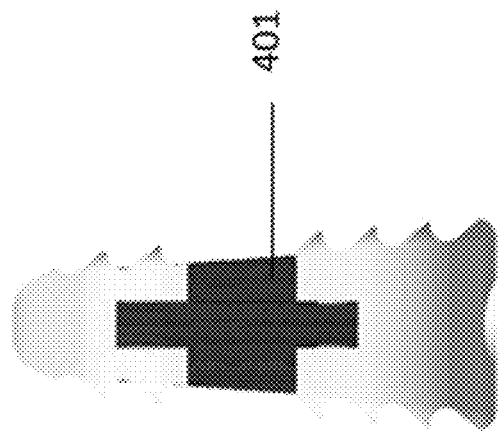
FIG. 4B is a top view of the embodiment of the implant device depicted in FIG. 4A.
Figure 4A:
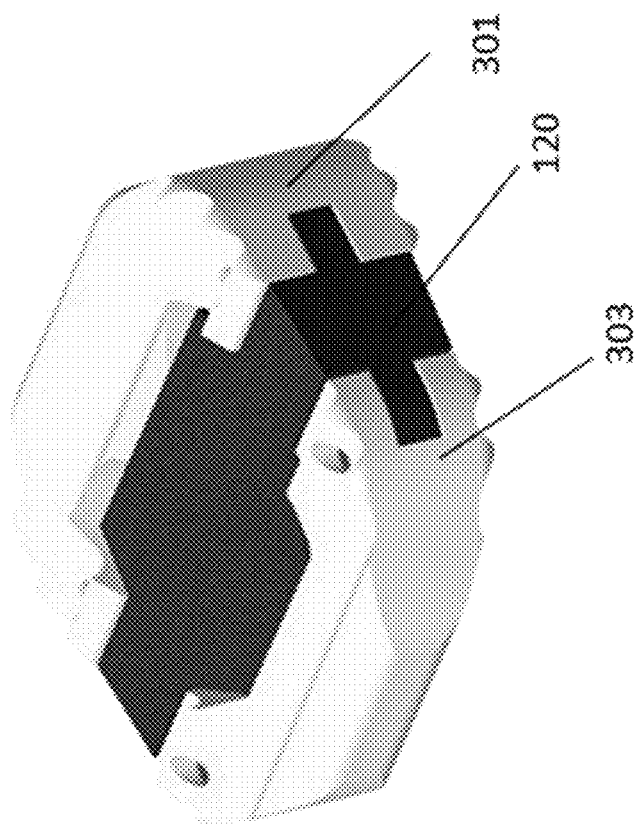
FIG. 4A is a perspective view of another embodiment of the implant device.

Complementary sections 301 and 303 may not connect to each other as shown in FIG. 4A and FIG. 4B. In this embodiment complementary sections 301 and 303 connect only to insert 120. Furthermore, side cut outs in complementary sections 301 and 303 may lead to the creation of cross shape 401. Complementary sections 301 and 303 in the form of the cross shape 40 in one embodiment form another locking mechanism of the present invention.

Figure 5A:
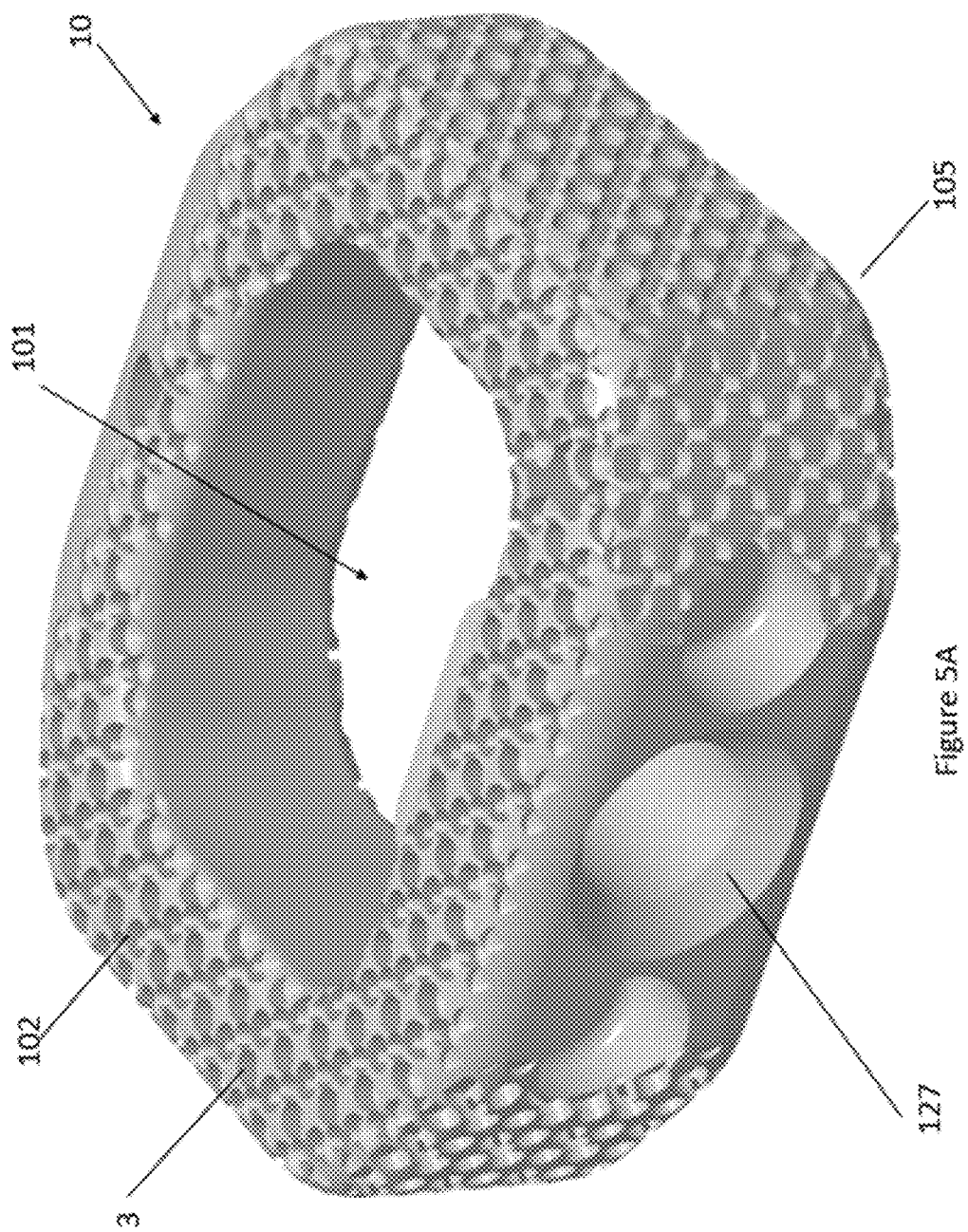
FIG. 5A is a perspective view of an alternative embodiment of the implant device.

FIG. 5A shows a perspective schematic of one embodiment of the device 10 related to the texture of body 105 discussed above. As shown in FIG. 5, the central opening 101 is surrounded by peripheral section 102. A plurality of holes 3 are formed on exterior surfaces of the implant, for example on the top, bottom, and sides of the peripheral section 102. A threaded opening 127, which extends through the front face of the peripheral section 102, allows the attachment of an insertion device. One threaded opening 127 is shown here, but the implant could be modified to work with multiple threaded openings or other types of insertion devices.

Figure 5B:
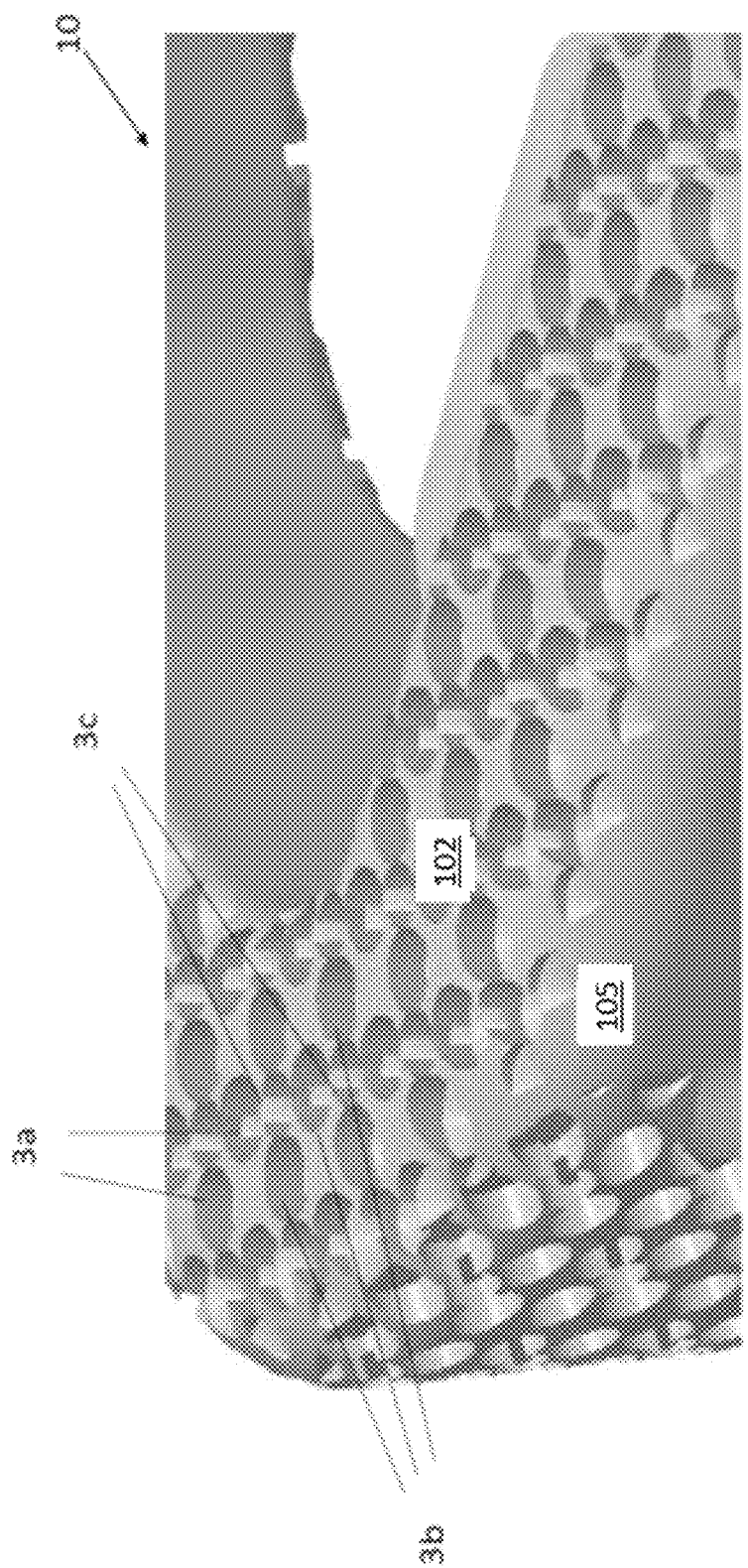
FIG. 5B is an enlarged view of a peripheral section of the implant device depicted in FIG. 5A.

FIG. 5B is an enlarged view of a peripheral section 102 of the implant device depicted in FIG. 5A showing first and second rows $3a$, $3b$ of holes having respective sidewalls through which interconnected openings $3c$ extend between holes on different rows (in this embodiment). The invention is not so limited, and the interconnected openings $3c$ can extend between holes on the same row and/or extend to holes separated from each other over multiple rows, as illustrated in FIG. 5A. FIG. 5B also shows that the holes 3 are blind holes formed in body 5. FIG. 5B also shows all the holes 3 having the same diameter, but the invention is not so limited and different diameter holes can be used on different rows or along the same raw. FIG. 5B also shows all the where interconnected openings $3c$ having the same width and depth, but the invention is not so limited and different diameter widths and depths can be used for the interconnected openings $3c$.

In one embodiment of the invention, holes 3 are formed with their central axis extending perpendicular to or within +/−10 degrees or within +/−20 degrees of or within +/−40 degrees of normal to the top or bottom surfaces of peripheral section 102. Similarly, in one embodiment, the sidewalls are formed with their vertical traces extending perpendicular to or within +/−10 degrees of or within +/−20 degrees of or within +/−40 degrees of normal to the top or bottom surfaces of peripheral section 102. Similarly, in one embodiment, the interconnected openings $3c$ are formed with their vertical traces extending perpendicular to or within +/−10 degrees of or within +/−20 degrees of or within +/−40 degrees of normal to the top or bottom surfaces of peripheral section 2.

In one embodiment of the invention, the sidewalls extend vertically downward from a top surface of the peripheral section 102 or extend vertically upward from a bottom surface of the peripheral section 102 along a constant pitch angle. In one embodiment of the invention, the sidewalls extend vertically downward from a top surface of the peripheral section 102 or extend vertically upward from a bottom surface of the peripheral section 102 along two or more constant pitch angles.

In one embodiment of the invention, the sidewalls can have contoured shapes with distinct interconnecting channels extending through the body material to connect one or more the holes together.

Accordingly, in one aspect of the present invention, the holes and/or the sidewalls have regular, machine-type formed surfaces with well-defined angles and intersections between the surfaces of the peripheral section 102 with the holes. This aspect would contrast to that pores or holes etched in to the surface forming dimples on the surfaces of the peripheral section 102.

In one embodiment of the invention, the interconnected openings 3c have a width between 100 to 1000 microns, 200 to 700 microns, 250 to 500 microns, and/or 300 to 400 microns (or any intervening ranges or values in between) for promoting bone growth in the interconnected openings 3c and in the holes 3.

In one embodiment of the invention, the holes 3 have a diameter from 100 to 10,000 microns, 500 to 7000 microns, 1000 to 5000 microns, or 2000 to 3000 microns (or any intervening ranges or values in between). In one embodiment of the invention, the holes 3 have a depth from 100 to 1000 microns, 200 to 700 microns, 250 to 500 microns, and/or 300 to 400 microns (or any intervening ranges or values in between).

Accordingly, in one embodiment of the invention, the implant comprises a body 105 with a peripheral section 102 and a central opening 101 that extends through the peripheral section 102. First and second rows of holes 3a, 3b are formed in an exterior surface of the peripheral section 102. As shown in FIG. 5B, the first hole has a first sidewall and defines a first cavity in the body portion while the second hole has a second sidewall and defines a second cavity in the body portion. The rows of holes 3a, 3b are arranged such that the first and second cavities are interconnected by interconnected openings 3c. The holes 3a, 3b and the interconnected openings 3c on external surface of the implant promote bone regrowth, especially when a bone graft material is included in the holes and the interconnected openings.

Figure 6:
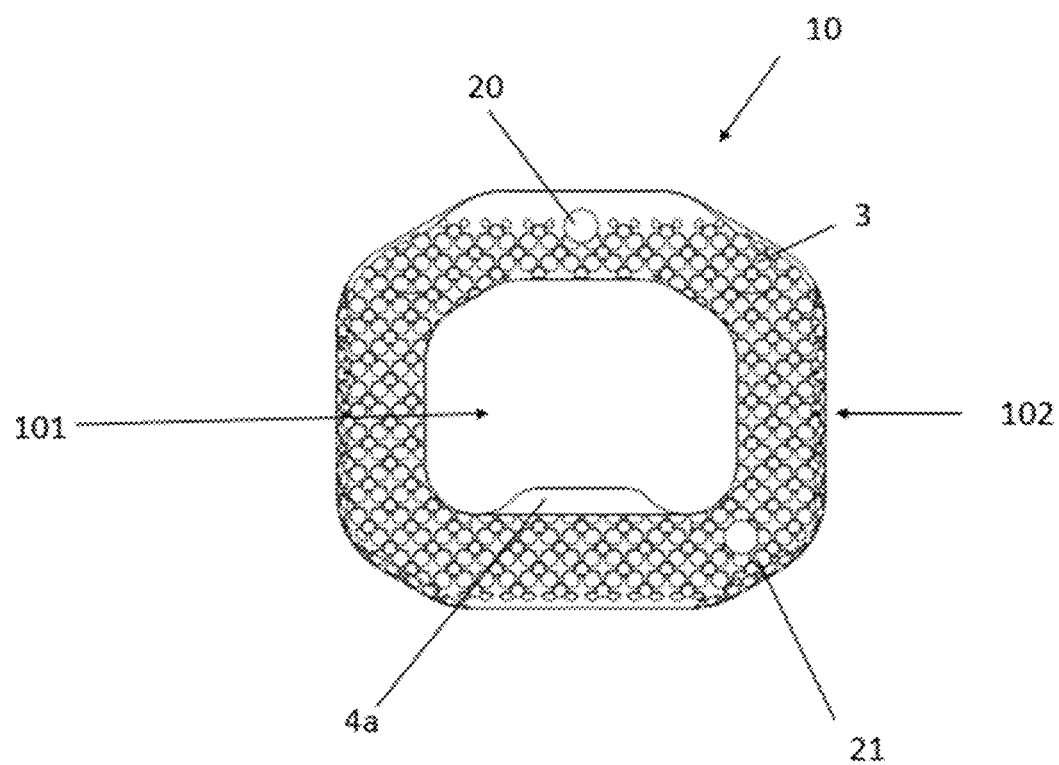
FIG. 6 is a top view of another embodiment of the implant device.

FIG. 6 is a top view of another embodiment of the device 110. As shown in FIG. 6, the top, sides, and bottom of the peripheral section 102 have a plurality of holes 3, which in this embodiment are overlapping holes with the region of overlap forming interconnected opening 3c as shown in FIG. 5b. As shown in FIG. 6, the holes have different diameters on different rows. The invention is not so limited, and the holes on different rows may have the same diameter. As shown in FIG. 6, a relief 4a extends into the central opening 101. Also shown, recesses 20 and 21 are provided which can accommodate metal beads herein, permitting the implant to be located during a radiographic scan.

Figure 7:
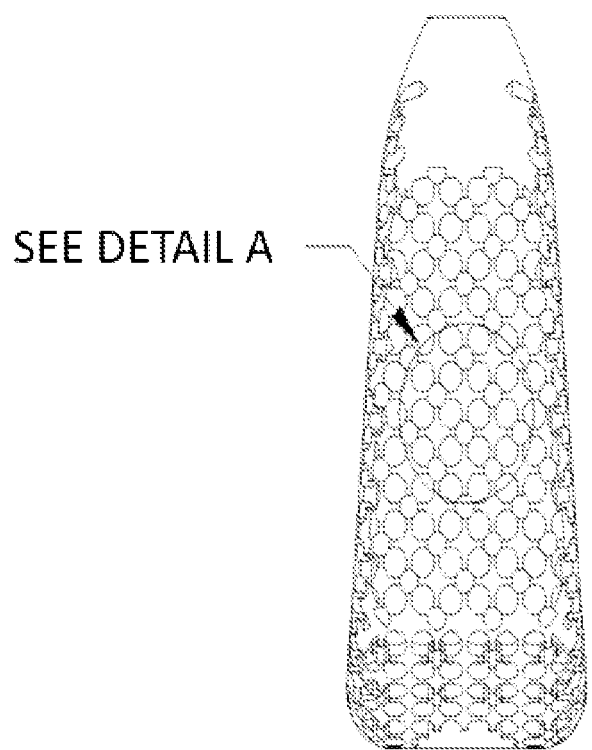
FIG. 7 is a side view of the implant device of FIG. 6.
Figure 8:
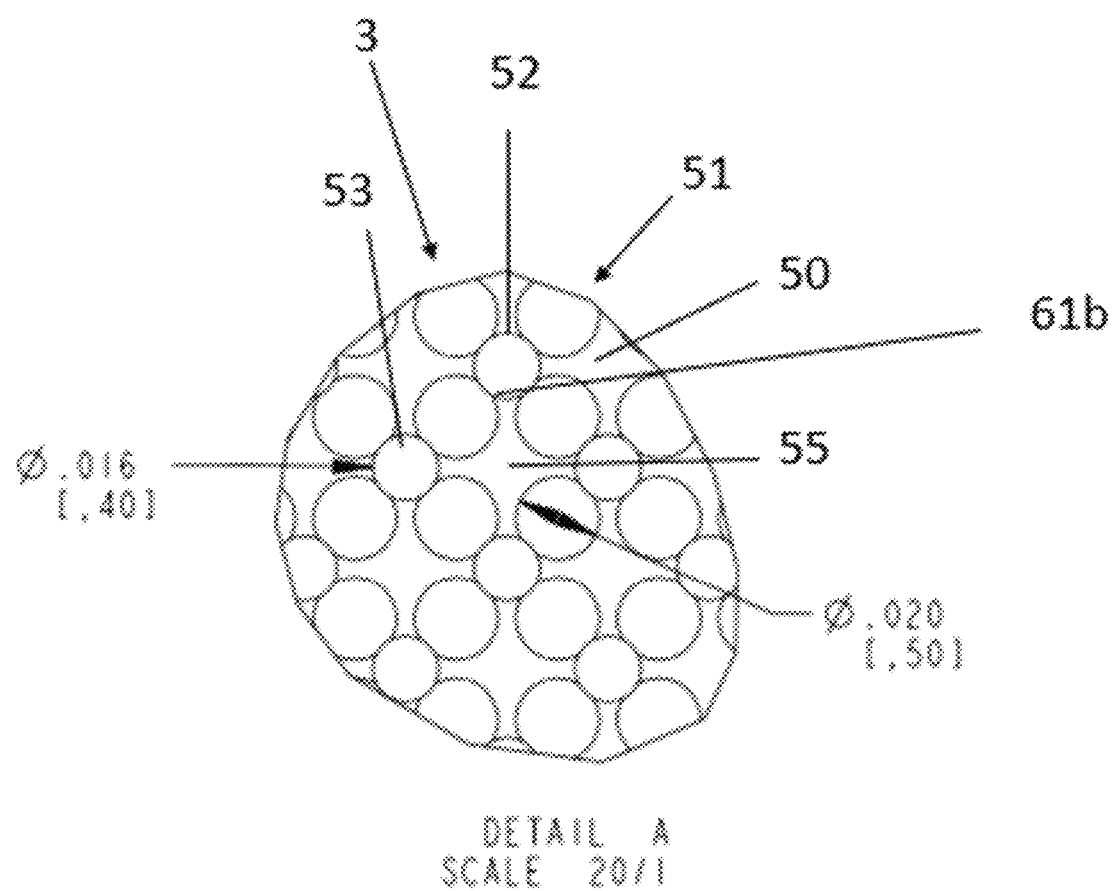
FIG. 8 is an expanded view of the interconnected openings of the implant device of FIG. 6.

FIG. 7 is a side view of the device shown in FIG. 6. In this embodiment, the height of the distal end 30 is smaller than the height of the proximal end 31. Similar to FIG. 5 and FIG. 6, the bottom top and sides of the peripheral portion 102 of the device in FIG. 7 can have a plurality of interconnected holes 3 which are (in one embodiment) all blind holes. FIG. 8 shows an expanded view of the implant device of FIG. 6. Arranged in rows, the interconnected blind holes define a cross-shaped region 50 in this example defined by four larger blind holes 51 that interconnect with smaller blind holes 52 or 53. The cross-shaped region 50 can be achieved by displacing the smaller blind holes 52 from each other by a distance greater than twice the diameter of the larger blind holes 51. The cross shaped solid section 55 is also present in this embodiment. In this embodiment, the holes connect due to overlap of their radii. In one embodiment, this pattern of connection extends throughout the entire peripheral portion. In one embodiment, some of the holes need not overlap, but rather could be interconnected as in FIG. 5B by a separate channel formed in the body of the implant to interconnect the holes.

Figure 9A:
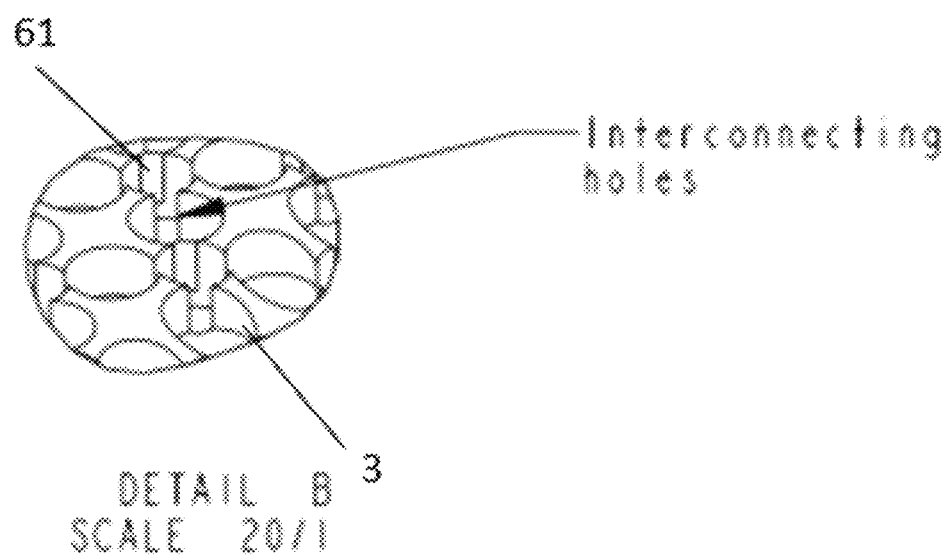
FIG. 9A is a perspective view of the interconnected openings according to another embodiment of the implant device.

The row arrangement and interconnecting openings (channels) 61 are illustrated in FIG. 9A. Here, smaller blind holes separate larger blind holes with the interconnecting channels 61 formed as a result of the overlap of one hole with the other. Although the channels 61 can be on the same plane (i.e., have the same depth) as the blind holes 3, the channels 61 can also be on a higher or lower plane (i.e., have a different depth than the blind holes 3).

Though not shown, in one embodiment of the invention, the insert 120 in FIG. 1 is inserted into a body 105 having the plurality of holes and interconnecting channels shown in FIGS. 5 through 9A.

Figure 9B:
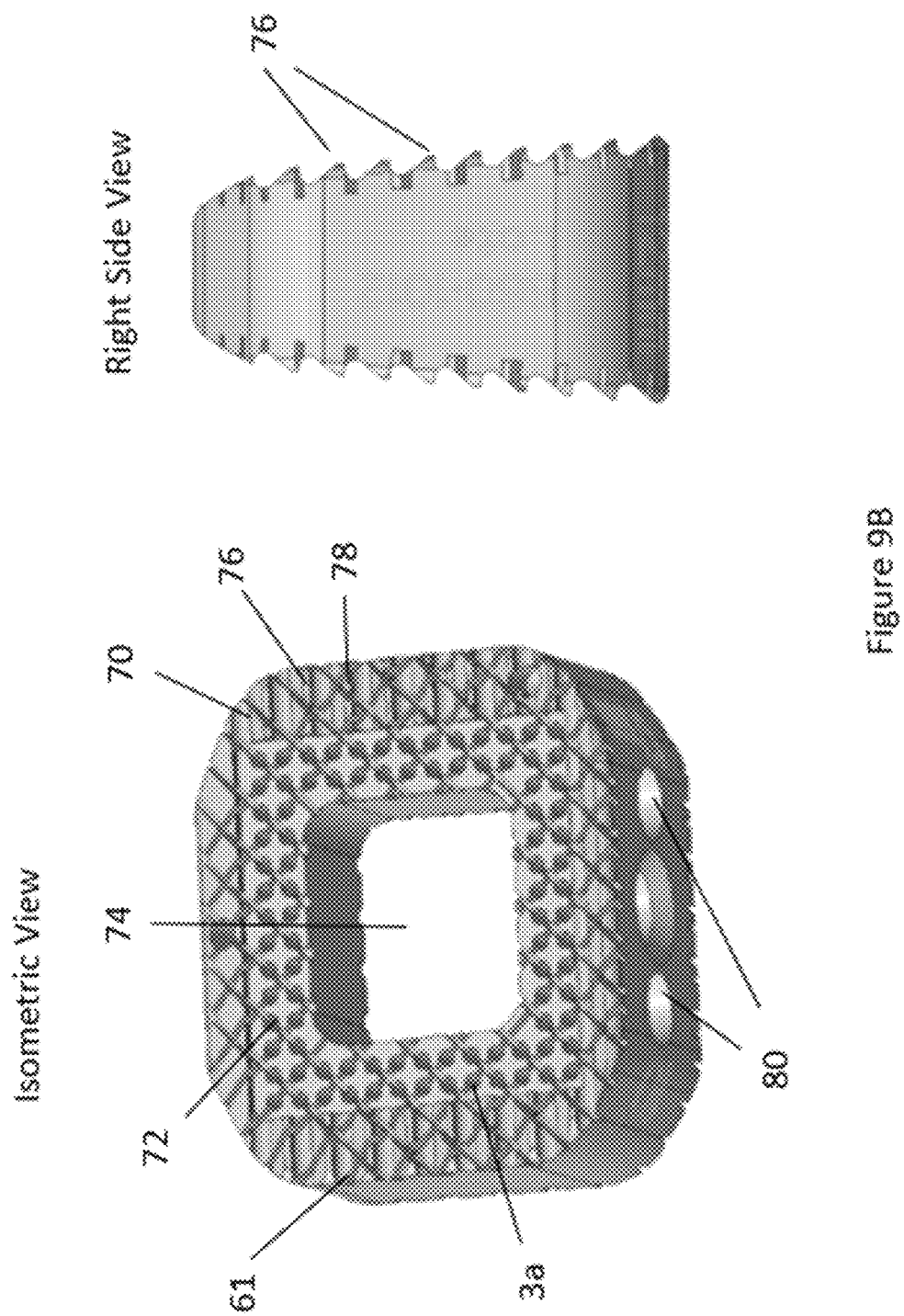
FIG. 9B is an illustration of another implant device according to another embodiment.

FIG. 9B is an illustration of another implant device according to another embodiment. In this embodiment, the channels 61 are formed in intersection directions. The boundary region 70 of the implant device does not have any holes while the interior region 72 (between the boundary region 70 and the central opening 74) has through holes 3a extending into a depth of the implant device. The right side view shown in FIG. 9B shows that, in one embodiment, the implant device is tapered with the widest section being on a side where an insertion device would connect to holes 80 on the side wall of the implant device.

Figure 9D:
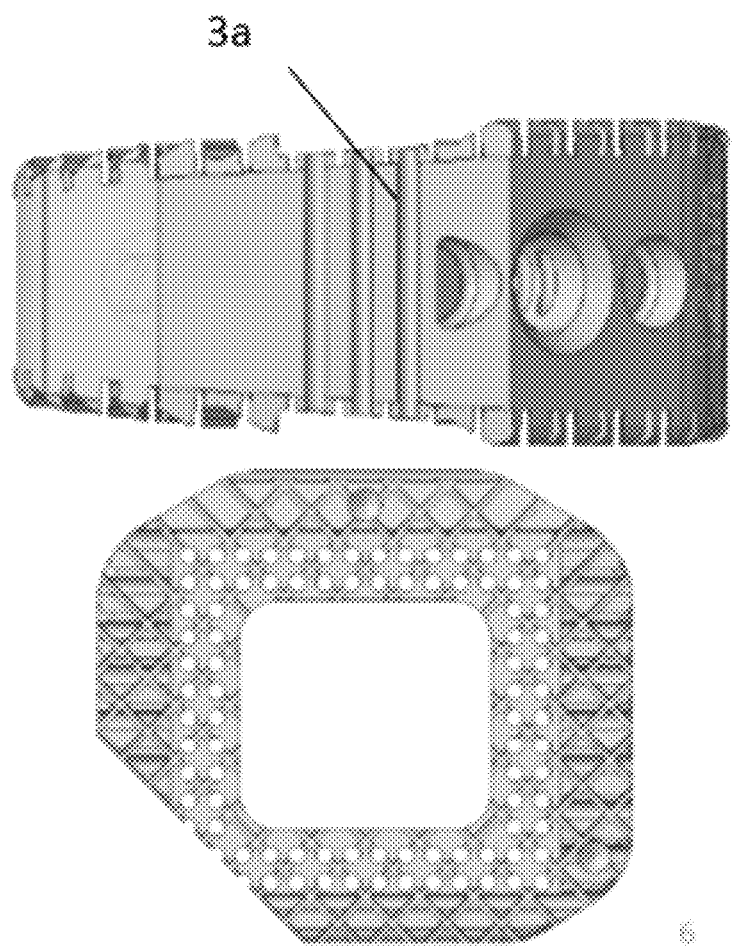
FIG. 9D is a cross sectional view of the implant device of FIG. 9B.

FIG. 9C is a top view of the implant device of FIG. 9B showing more clearly the intersecting channels 61 and the through holes 3a. FIG. 9D is a cross sectional view of the implant device of FIG. 9B showing the through holes 3a extending across a depth of the implant device.

Figure 9E:
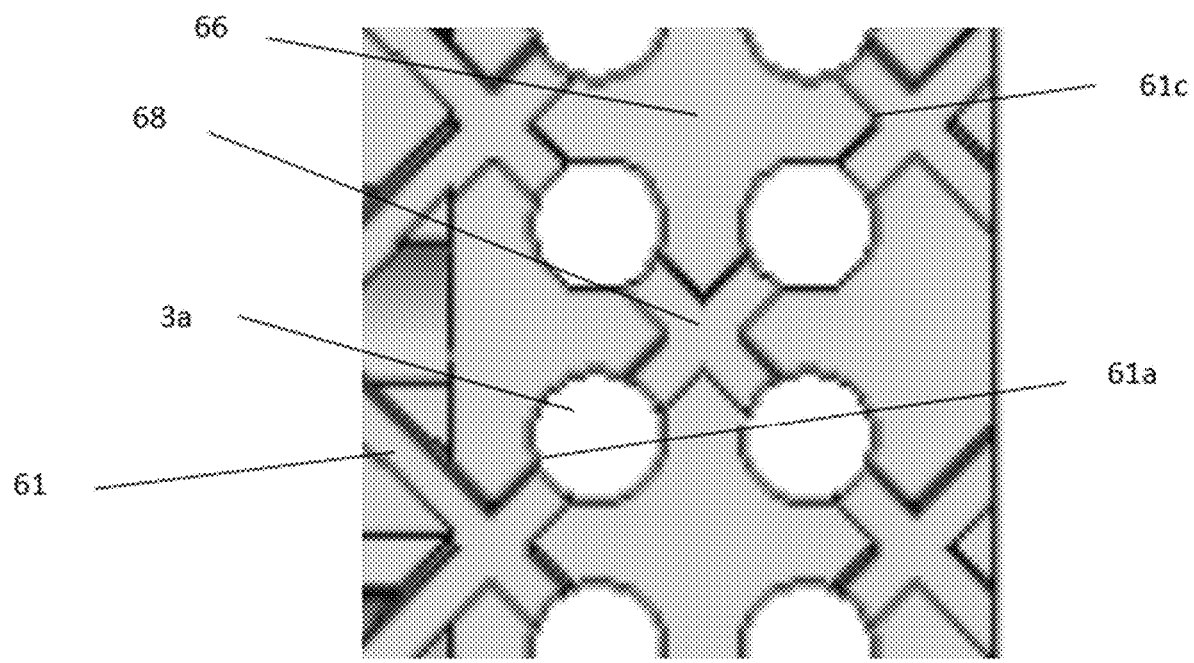
FIG. 9E is an enlarged view of the implant device of FIG. 9B.

FIG. 9E is an enlarged view of the implant device of FIG. 9B. Here, one aspect of the invention is the construction formed where the channels 61 intersect the through holes 3a. This construction forms surface wall which has a vertical edge 61a with two opposing surfaces, one planar along the cut forming the channel 61 and one curved surface along the hole 3a. This aspect in one embodiment of the invention is advantageous for bone in-growth. In general, the vertical edge 61a may have two opposing surfaces, one planar surface along the interconnected opening and one curved surface along the first cavity, as shown in FIG. 9E. However, the present invention is not so limited, and a vertical edge can be formed by overlapping of the holes 3a without there being a channel 61. In this case, a vertical edge 61b is formed from two opposing curved surfaces (see edge 61b in FIG. 8). Similarly, vertical edges can be formed in the body portion of the implant device by the intersection of the channels 61. In this case, the vertical edge (see edge 61c in FIG. 9E) is formed from two plane opposing surfaces.

FIG. 9F is a scaled drawing of the implant device of FIG. 9B with the dimensions shown in millimeters. The view in FIG. 9F is that of a vertical cut through the right-had side view shown in FIG. 9B.

In one embodiment of the invention, the channels 61 have a width between 100 to 1000 microns, 200 to 700 microns, 250 to 500 microns, and/or 300 to 400 microns (or any intervening ranges or values in between) for promoting bone growth in the channels 61 and in the holes 3a.

In one embodiment of the invention, the body portion comprises a cross shaped solid section 66 (as shown in FIGS. 9C and 9E) extending in a region of the body portion and bounded by four holes in the body portion.

In one embodiment of the invention, intersecting channels 68 (as shown in FIGS. 9C and 9E) are formed in the body portion where one of the intersecting channels comprises the interconnected opening.

In one embodiment of the invention, the intersecting channels 68 connect between four holes in the body portion.

In one embodiment of the invention, the body portion comprises a set of regularly spaced six holes with an "X" pattern of interconnection channels between first set of the six holes and with a cross shaped body portion between a second set of the six holes, the set repeating as a unit across the body portion In one embodiment of the invention, there are corrugations 76 (as shown in FIG. 9B) formed on an outermost region of the body implant not having any holes therein. In one embodiment of the invention, the corrugations comprise teeth on the body portion with diagonal cuts 78 (as shown in FIG. 9B) formed therethrough the teeth by the intersecting channels, and optionally the teeth extend above a surface of the body portion containing the first hole and the second hole.

While not being constrained by theory, the porous bodies of this invention are believed to increase the speed of bone ingrowth and vertebra fusion by stimulating bone to grow into the holes or porous titanium as well as the channels in-between. By stimulating bone growth into connecting channels, the implant increases the speed of bone growth into adjacent holes. The strength of the vertebra fusion is also increased as bone is likely to continue growing through the channel or porous titanium and connect the implant and the bone together.

FIGS. 9G-9J are perspective views of other implant devices of the invention having a porous structure similar to those structures described above, whose details will not be repeated in as much detail here as above but with similar reference numbers referring to similar elements and having similar attributes to those described above.

In FIGS. 9G-9J, channels 61 are formed in intersection directions in the boundary region 70. The boundary region 70 does not have any holes (such as through holes 3*a*) while the interior region 72 (between the boundary region 70 and any of the central openings 74) has through holes 3*a* extending into a depth of the implant device. Intersecting channels 68 (similar to those shown in FIGS. 9C and 9E) are formed in the body portion where one of the intersecting channels comprises an interconnected opening (as discussed above). Furthermore, the body portion can include a cross shaped solid section 66 (similar to that shown in FIGS. 9C and 9E) extending in a region of the body portion and bounded by four holes 3 in the body portion.

In FIGS. 9G-9J, the porous surface structures (such as blind holes 3, through holes 3*a*, 3*b*, interconnected openings 3*c*, blind holes 51, 52, 53, channels 61, channels 68, and the respective intersections of these channels) in the body portions and/or in the boundary region 70 are characterized by having an average dimension between 100-1000 microns, preferably between 200 and 750 microns, and more preferably between 300 and 700 microns, with a particular range of 380-650 microns of note for permitting the porous implants of the present invention to wet fluids into the porous structures of this design. In one embodiment of the invention, the through holes 3*a* in the interior region 72 having a diameter in the size of 380-650 microns is particular useful in wetting a fluid up through the holes 3*a* permitting fluid (such as bodily fluids including blood) in contact with a bottom side of the implant to migrate to the top side, where it will spread laterally across the surface of the implant. Once implanted, any nutrients or bone growth factor components in a patient's blood would be in fluid communication with all the porous surface structures by way of the wetted structure, thereby promoting bone regrowth.

The average dimensions noted above are consistent with the above noted dimensions of the interconnected holes having a width or diameter between 100 to 1000 microns, 200 to 800 microns, 250 to 700 microns, and/or 300 to 600 microns (or any intervening ranges or values in between). The average dimensions noted above are consistent with the above noted dimensions of the pore sizes for implant of insert 120 which was described above to be on the order of approximately 400-600 μm, or also as being between 100 to 1000 microns, 200 to 800 microns, 250 to 700 microns, 300 to 600 microns, about 0.1 mm to about 5 mm, about 0.5 mm to about 3 mm, or about 1 mm to about 2 mm (or any intervening ranges or values in between). The average dimensions noted above are consistent with the above noted dimensions of channels 61 having a width between 100 to 1000 microns, 200 to 700 microns, 250 to 500 microns, and/or 300 to 400 microns (or any intervening ranges or values in between).

Figure 9G:
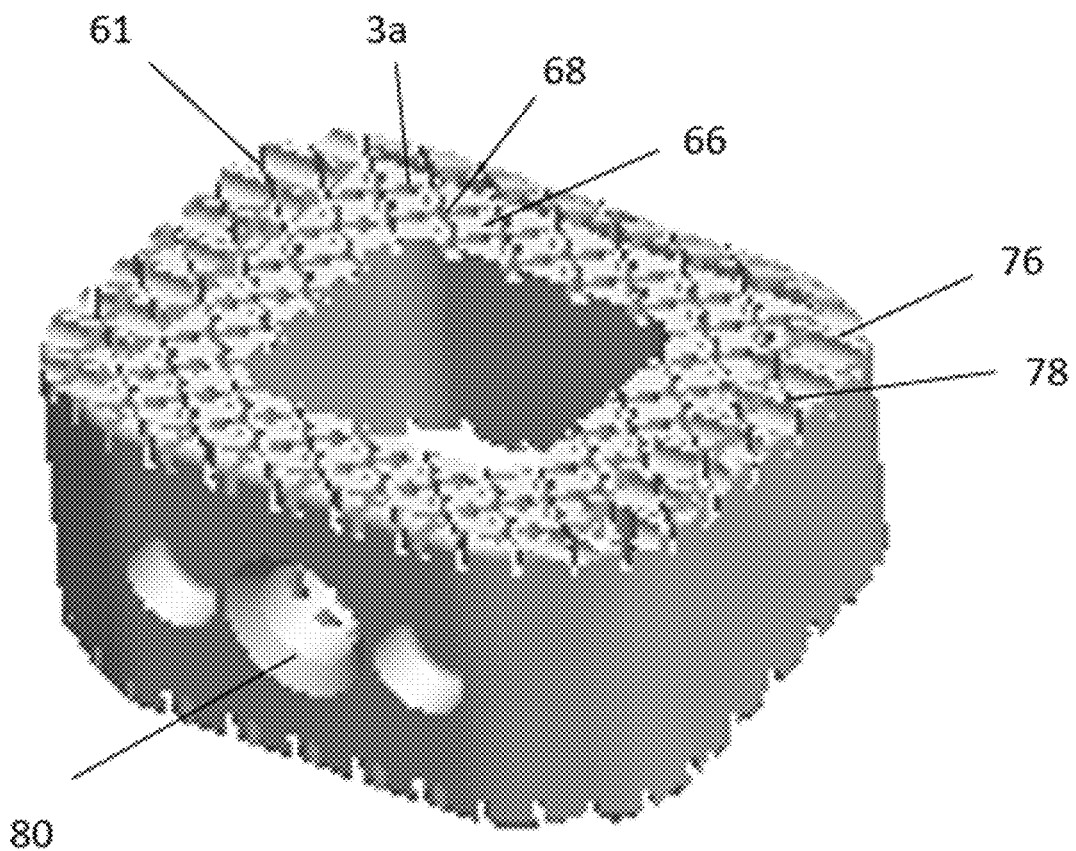
FIG. 9G is a perspective view of another implant device of the invention.

In FIGS. 9G-9H, there are corrugations 76 (similar to those shown in FIG. 9B) formed on the outermost boundary region 70 of the body implant not having any holes therein. Such corrugations could be included in the implants of FIGS. 9I-9J. In FIGS. 9G-9H, the corrugations 76 comprise teeth on the body portion with diagonal cuts 78 (similar to those shown in FIG. 9B).

Figure 9I:
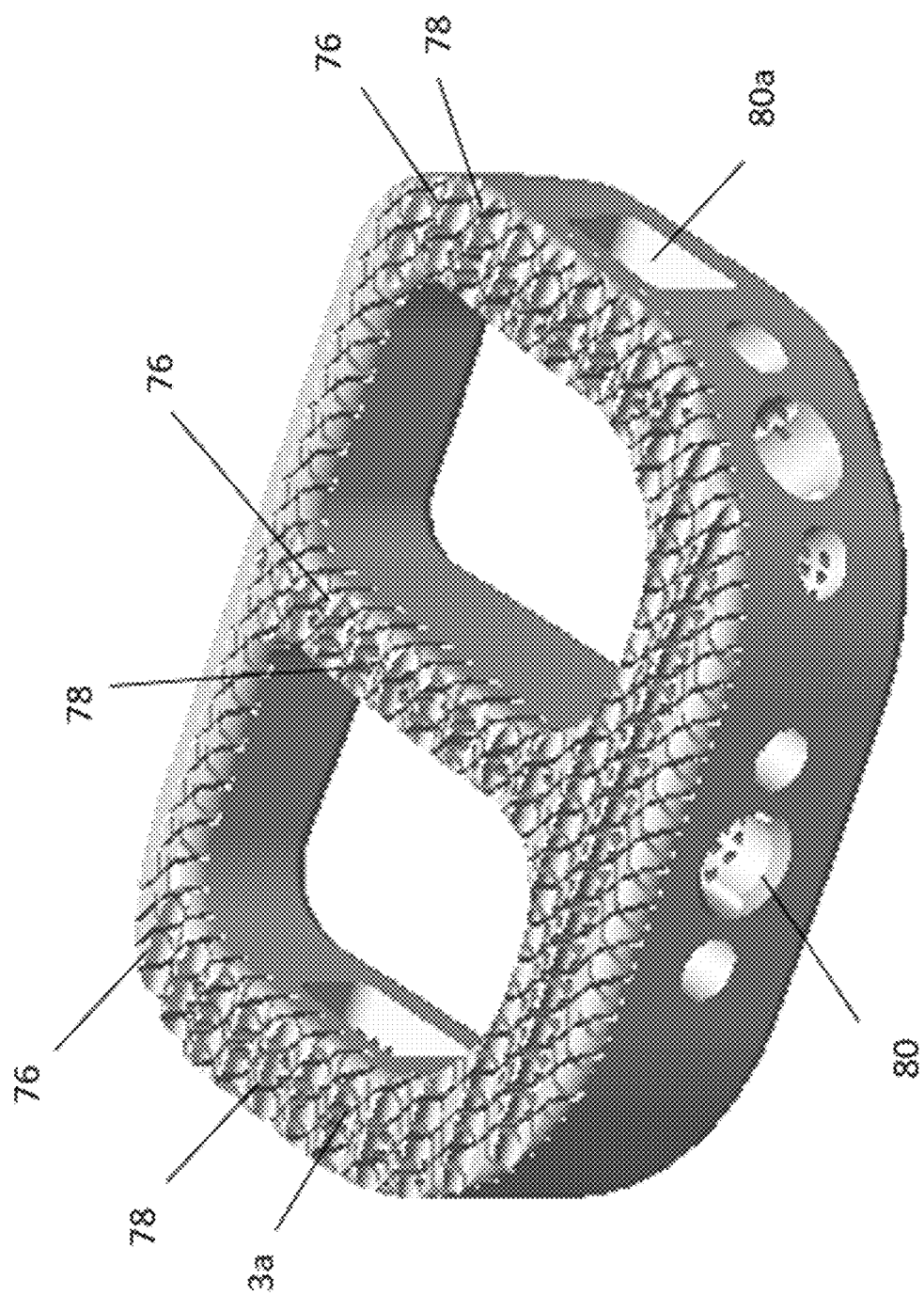
FIG. 9I is a perspective view of a further implant device of the invention.

For the implant of FIG. 9G. this implant has a taller aspect ratio of height to lateral width and length than the other ones shown in this disclosure. Implant of FIG. 9G is intended for use in the cervical region of the spine. For the implant of FIG. 9H. this implant has a narrower aspect ratio of width to length than the other ones shown in this disclosure while having a tapered height increasing height toward the distal end. Implant of FIG. 9H is intended for use in the lumbar region of the spine, using a posterior approach. For the implant of FIG. 9I. this implant has two central openings with a center sidewall between the openings and connecting the distal and proximal ends of the implant together. The implant of FIG. 9I represents another embodiment of the invention where nearly all faces of the implant have corrugations 76 thereon. The implant of FIG. 9I also represents another embodiment of the invention where the through holes 3*a* are included in the region with the corrugations 76. Implant of FIG. 9I is intended for use in the lumbar region of the spine, using an anterior approach. For the implant of FIG. 9J. this implant is a non-tapered implant with an elongated central opening. The implant of FIG. 9J represents another embodiment of the invention where all faces of the implant have corrugations 76 thereon. The implant of FIG. 9J (like the implant of FIG. 9I) has through holes 3*a* included in the region with the corrugations 76. Implant of FIG. 9J is intended for use in the lumbar region of the spine, using a lateral approach.

In FIGS. 9H-9J, there are sidewall openings 80*a* (different from opening 80 utilized for the insertion device) disposed between the upper and lover faces of the implant where the corrugations 76 are disposed. The openings 80*a* permit bone graft material flow throughout the interior region of the implants.

The implants of the present invention can be composed of any applicable biocompatible material either currently known or unknown. It can also be constructed by any means known in the art such as but not limited to machining, injection molding, or lithographic etching. The implant can also be constructed by pressing indentations into a green or partially green body portion mold and then curing the mold.

The implant can be of any size. An embodiment can be 5-12 mm high and have a lordotic angle of 0 or 5-10 degrees. Some embodiments could have footprints of 12 mm×14 mm, 13 mm×15 mm, or 14 mm×16 mm. Some embodiments will have degrees of 6 or 10.

Any embodiment of the implant could be packaged in a kit including an insertion device. Such an example with implant 81 and an insertion device 82 is shown in FIG. 10.

Though not shown it is entirely possible to combine the insert 120 in FIG. 1, 2, 3, or 4 with the first and second rows of holes 3a 3b shown in FIG. 5, the plurality of holes 6 shown in FIG. 6, the taper shown in FIG. 7, the cross shaped region in FIG. 8 or the row and interconnecting openings in FIG. 9A.

Figure 11:
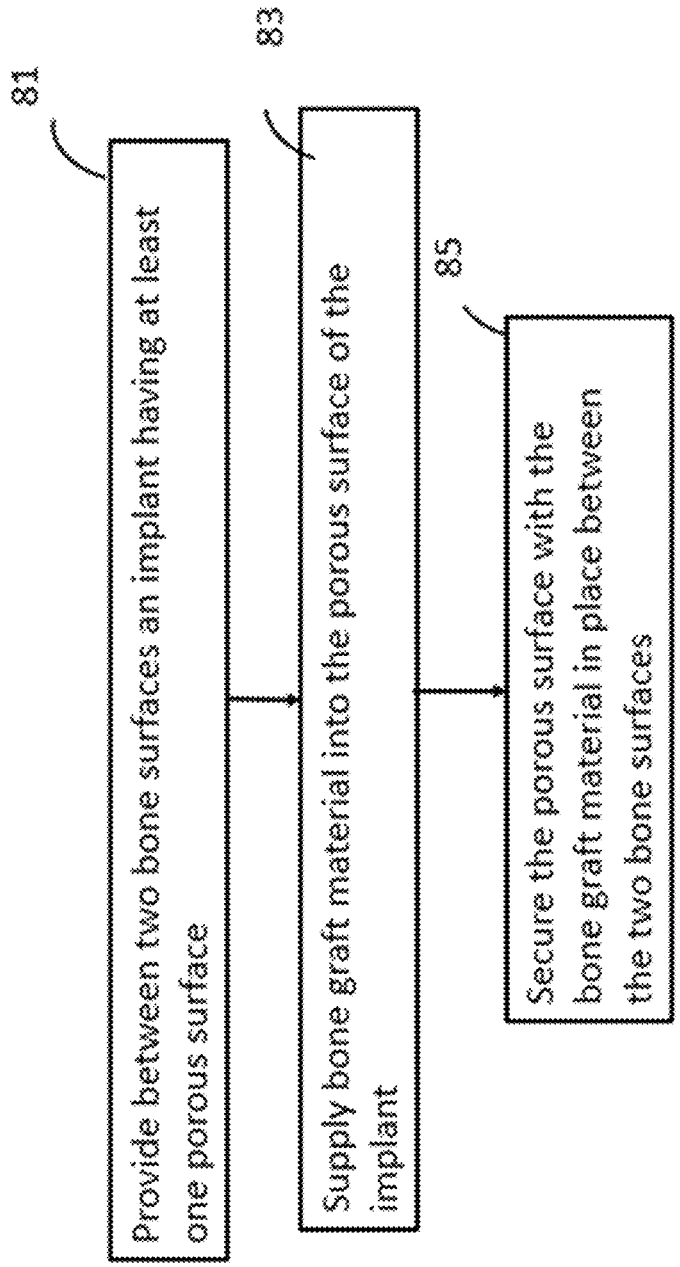
FIG. 11 is a flow diagram explaining a method of the present invention.

FIG. 11 is a flow diagram explaining a method of the present invention. In one embodiment, a method of use for example secures two bones surfaces together. At 81, an implant (such as any of the implants described above) is provided between two bone surfaces. The implant has at least one porous surface. At 83, a bone graft material is supplied into the porous surface. At 85, the porous surface with the implant is secured in place between two bone surfaces.

Figure 12:
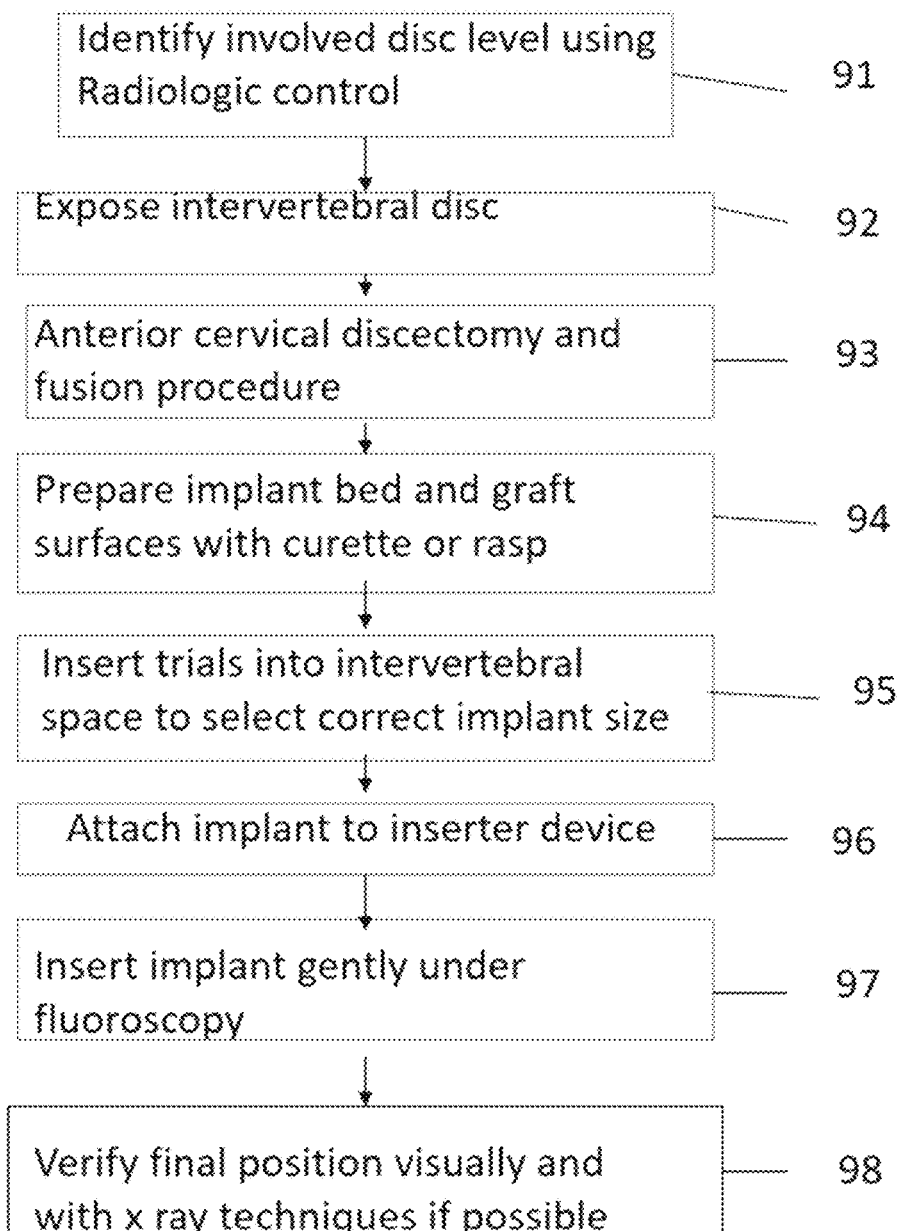
FIG. 12 is a flow diagram explaining a method of the present invention.

A method of use is also outlined in FIG. 12. At 91, the involved disc level is identified through radiologic control. At 93, anterior cervical approaches are used for intervertebral disc exposure. At 94, after anterior cervical discectomy, a fusion procedure is performed, a curette or rasp is used to prepare the implant bed and graft surfaces. At 95, the correct implant size is selected by inserting trials into the intervertebral space. At 96, once the proper size implant is selected, it is attached to an inserter instrument such as insertion tool 82. In some embodiments of the invention, the implant is then filled with an autograft material. At 97, the implant is inserted under fluoroscopy into the disc space once mounted on the insertion tool. In some embodiments of the invention, a tamp is used to secure the device in its final position. At 98, the final position of the implant is verified visually and/or alternatively using x-ray techniques. A supplemental fixation system may then be applied.

The implant may be later removed. This can be accomplished by attaching the inserter to the implant anteriorly and removing the implant from the disc space. A cobb elevator or an osteotome can be used to loosen the implant from the bone if needed.

This invention is not limited to a specific type of bone graft or autograft material. In general, a variety of bone graft materials are known and suitable for this invention. These typically comprise calcium phosphate-based or gel-based materials. Polymer-based bone graft substitutes containing (or not containing) collagen can be used. Ceramic bone graft substitutes can be used. In one embodiment, the implantable bone graft material comprises a composite of a ceramic and a polymer. The ceramic and the polymer can be present at a weight ratio ranging from about 10:1 ceramic to polymer to about 2:1 ceramic to polymer. Alternatively, the weight ratio of the ceramic to the polymer can range from about 2:1 (about 66% ceramic to about 33% polymer), from about 3:1 (about 75% ceramic to about 25% polymer), from about 4:1 (about 80% ceramic to about 20% polymer), from about 9:1 (about 90% ceramic to about 10% polymer), from about 10:1 (about 99% ceramic to about 1% polymer). Other bone graft materials besides those specifically listed above can be used.

This invention is also not limited to the type of material that the implant is made of. The implants of this invention can be made of any material appropriate for human implantation and having the mechanical properties sufficient to be utilized for the intended purpose of spinal fusion, including various metals such as cobalt chrome, stainless steel or titanium including its alloys, various plastics including those which are bio-absorbable, and various ceramics or combination sufficient for the intended purpose. In one embodiment, the implant is made of medical grade PEEK (Polyetheretherketone). Further, the implants of this invention may be made of a solid material, a mesh-like material, a porous material and may comprise, wholly or in part, materials capable of directly participating in the spinal fusion process, or be loaded with, composed of, treated of coated with chemical substances such as bone, morphogenic proteins, hydroxyapatite in any of its forms, and osteogenic proteins, to make them bioactive for the purpose of stimulating spinal fusion. The implants of this invention may be wholly or in part bioabsorbable. Other materials for the implant device besides those specifically listed above can be used.

This invention is also not limited to the methods by which the implants are made. The individual components can be machined from solid stock pieces. Molding can be used to make the individual components. In this case, machining to final dimensions may or may not be in order. The surfaces once properly dimensioned can be coated with a variety of biocompatible coatings and/or surface treatments. Various coatings include for example calcium phosphate ceramics, such as tricalcium phosphate (TCP) and hydroxyapatite (HA), and hydroxyapatite (a naturally occurring material in bone). Moreover, If the implant is not made of bone, surfaces of the implant that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces of the implant.

In one embodiment of the invention, the holes and interconnecting openings described above can be machined into the body portion. In one embodiment of the invention, the holes and interconnecting openings described above can be pressed into or formed with an uncured mold of the body portion after which the uncured mold is cured. In one embodiment of the invention, the holes and interconnecting openings described above can be lithographically formed by etching the body portion.

In some embodiments, any of the implants and instruments described above (such as the insertion tool) can be used with additional implants and instruments. In some embodiments, the implants and instruments can be used with stabilization members, such as plates, screws, and rods. In addition, a multi-level construct can be formed, wherein any one or more of the implants 20 described above can be used on one level, while a similar or different implant (e.g., fusion or prosthetic) can be used on a different level.

This invention is also not limited to the shapes and designs noted above.

Generalized Statements of the Invention:

The following numbered statements describe generalized aspects or embodiments of the invention and are provided for illustrative purposes.

Statement 1. A surgical implant comprising: a body having at least one interior surface, the body forming a peripheral support for the implant; a porous insert comprised of a porous material, having an axially-extending hole, and attached to the body (e.g., along the at least one interior surface such that the porous material extends across a height of the body); and the porous insert comprising a locking mechanism formed in the porous insert or extending from the porous insert, the locking mechanism minimizing movement of the porous insert within the body. In one aspect of the invention, the porous insert preferably does not extend beyond an uppermost surface of the body and is not a substantial load bearing member. In one aspect of the invention, the body is preferably, but not necessarily, non-porous and made of material different than the porous insert. Indeed, in one aspect of the invention, the body can be made of the same material as the porous insert. In one aspect of the invention, the body is preferably, but not necessarily, a separate piece from the porous insert. Indeed, in one aspect of the invention, the body and the porous insert could be made at the same time by a three-dimensional printing process making the body and the porous insert a singular piece in which the locking mechanisms may or may not be also formed at the same time. For example, the body and the porous insert could be made at the same time by a three-dimensional printing process by which respective holes are formed in the body and the porous insert for acceptance of pin 125. For example, the body and the porous insert could be made at the same time by a three-dimensional printing process by which the thin-walled sections 231 and 233 in an interlocked state engaging and contacting recesses 240 would be formed.

Statement 2. The implant of statement 1, wherein the porous body comprises a plurality of interconnected holes extending throughout a section of the porous insert.

Statement 3. The implant of statement 2, wherein the interconnected holes are of a predefined size.

Statement 4. The implant of statement 2, wherein the interconnected holes extend linearly across the section of the porous insert.

Statement 5. The implant of statement 2, wherein the interconnected holes extend linearly and diagonally across the section of the porous insert.

Statement 6. The implant of any of the statements above (or a combination thereof), wherein the porous insert is three-dimensionally printed.

Statement 7. The implant of any of the statements above (or a combination thereof), wherein the porous insert is enclosed by the peripheral support of the body.

Statement 8. The implant of any of the statements above (or a combination thereof), wherein the porous insert is partially enclosed by the peripheral support of the body.

Statement 9. The implant of any of the statements above (or a combination thereof), wherein the body comprises two sections, and the porous insert contacts the two sections of the body.

Statement 10. The implant of any of the statements above (or a combination thereof), wherein the porous insert comprises an upper insert and a lower insert.

Statement 11. The implant of statement 10, wherein at least one of the upper insert and the lower insert have a flange which contacts a laterally-extending interior surface of the body.

Statement 12. The implant of any of the statements above (or a combination thereof), wherein the locking mechanism comprises a projection from the porous insert which engages in a recess in the body.

Statement 13. The implant of any of the statements above (or a combination thereof), wherein the locking mechanism comprises a cross-channel in the porous insert accepting a flange extending from the body toward the porous insert.

Statement 14. The implant of any of the statements above (or a combination thereof), wherein the cross-channel traverses the porous insert laterally.

Statement 15. The implant of any of the statements above (or a combination thereof), wherein the cross-channel traverses the porous insert axially.

Statement 16. The implant of any of the statements above (or a combination thereof), wherein the locking mechanism comprises a pair of projections of the porous material from the porous insert engaging around a flange of the body.

Statement 17. The implant of any of the statements above (or a combination thereof), wherein the locking mechanism comprises a through-channel in the porous insert accepting a flange extending from the body toward the porous insert.

Statement 18. The implant of any of the statements above (or a combination thereof), wherein the locking mechanism comprises a hole in the porous insert configured for accepting a pin connecting the body to the porous insert.

Statement 19. The implant of any of the statements above (or a combination thereof), wherein the porous insert slides longitudinally into place between two complementary sections of the body.

Statement 20. The implant of any of the statements above (or a combination thereof), wherein the porous insert slides vertically into place between the two complementary sections.

Statement 21. The implant of any of the statements above (or a combination thereof), wherein the body comprises polyetheretherketone (PEEK).

Statement 22. The implant of statement 21, wherein the PEEK comprises carbon fibers present in a weight percentage of the component of about 5 to 75%.

Statement 23. The implant of any of the statements above (or a combination thereof), wherein the porous insert comprises a plurality of interconnected holes extending throughout a section of the porous insert.

Statement 24. The implant of any of the statements above (or a combination thereof), wherein the porous material comprises porous titanium.

Statement 25. The implant of statement 24, wherein the porous titanium is formed by a three-dimensional printing process.

Statement 26. The implant of statement 25, wherein the porous titanium has a plurality of interconnected holes extending throughout a section of the porous insert.

Statement 27. The implant of statement 26, wherein the interconnected holes extend linearly across the section of the porous insert.

Statement 28. The implant of statement 26, wherein the interconnected holes extend linearly and diagonally across the section of the porous insert.

Statement 29. The implant of any of the statements above (or a combination thereof), wherein the body is tapered with a smaller height toward a posterior side and a greater height toward an anterior side.

Statement 30. The implant of statement 29, wherein a lateral extending edge on at least one of the posterior side or the anterior side comprises a rounded edge.

Statement 31. The implant of any of the statements above (or a combination thereof), further comprising teeth present on a surface of the body as corrugations.

Statement 32. A kit comprising: the surgical implant of any of statements 1-31 (or combinations thereof); and an intervertebral insertion device.

Statement 33. A method for securing two bones surfaces together, comprising: providing between two bone surfaces the surgical implant of any of statements 1-31 (or combinations thereof) including the porous insert; supplying bone graft material into the surface of the porous implant; and securing the porous surface with the bone graft material in place between the two bone surfaces.

Statement 34. The method of statement 33, wherein providing comprises locking an extrusion of the porous insert into the body to prevent the porous insert from moving within the body.

Statement 35. A surgical implant comprising:
a body portion comprising a first hole formed in the exterior surface thereof, a second hole adjacent the first hole, and a central opening extending through the body portion, wherein
the first hole has a first sidewall and a first cavity in the body portion,
the second hole has a second sidewall and a second cavity in the body portion, and
the first cavity and the second cavity have an interconnected opening there between.

Statement 36. The surgical implant of statement 35, wherein the interconnected opening comprises a surface channel formed in the surface of the body portion for interconnecting the first cavity and the second cavity together.

Statement 37. The surgical implant of any of the statements above below statement 35 (or a combination thereof), wherein the interconnected opening is formed by an overlap of the first hole with the second hole.

Statement 38. The surgical implant of any of the statements above below statement 35 (or a combination thereof), wherein the interconnected opening comprises a vertically-extending slot in at least one of the first sidewall and the second sidewall.

Statement 39. The surgical implant of any of the statements above below statement 35 (or a combination thereof), wherein at least one of the first hole and the second hole comprises a blind hole or a through hole.

Statement 40. The surgical implant of any of the statements above below statement 35 (or a combination thereof), wherein the first hole comprises a first plurality of first blind holes, and the second hole comprises a second plurality of second blind holes, or wherein the first hole comprises a first plurality of first through holes, and the second hole comprises a second plurality of second through holes.

Statement 41. The surgical implant of any of the statements above below statement 35 (or a combination thereof), wherein the body portion comprises a biocompatible material for permitting tissue in-growth in the first cavity, the second cavity, and the interconnected opening.

Statement 42. The surgical implant of any of the statements above below statement 35 (or a combination thereof), wherein the body portion is tapered such that a first height of the body portion at a distal end is smaller than a second height at a proximal end.

Statement 43. The surgical implant of any of the statements above below statement 35 (or a combination thereof), wherein the first hole comprises a first row of first holes, and the second hole comprises a second row of second holes.

Statement 44. The surgical implant of statement 43, wherein the first holes have a larger diameter than the second holes Statement 45. The implant of statement 43, wherein, in the second row, one of the second holes is disposed offset and centered with respect to one of the first holes in the first row.

Statement 46. The surgical implant of statement 43, wherein, in the second row, one of the second holes is displaced from one of the first holes a distance greater than two diameters of the first holes.

Statement 47. The surgical implant of statement 43, wherein the interconnected opening is formed by an overlap of one of the second holes with one of the first holes.

Statement 48. The surgical implant of statement 43, wherein the body portion comprises a cross-shaped solid section extending between the plural second holes in different rows.

Statement 49. The surgical implant of any of the statements above below statement 35 (or a combination thereof), wherein the body portion comprises a cross shaped solid section extending in a region of the body portion having no holes.

Statement 50. The surgical implant of any of the statements above below statement 35 (or a combination thereof), wherein the first hole and the second hole comprise holes machined into the body portion.

Statement 51. The surgical implant of any of the statements above below statement 35 (or a combination thereof), wherein the first hole and the second hole comprise holes pressed into or formed with an uncured mold of the body portion after which the uncured mold is cured.

Statement 52. The surgical implant of any of the statements above below statement 35 (or a combination thereof), wherein the first hole and the second hole comprise holes lithographically formed by etching the body portion.

Statement 53. The surgical implant of any of the statements above below statement 35 (or a combination thereof), wherein the body portion is configured to fit between two vertebrae.

Statement 54. The surgical implant of any of the statements above below statement 35 (or a combination thereof), wherein the body portion comprises a sidewall having one or more apertures for holding the body portion to an intervertebral insertion device for insertion of the implant between two vertebrae.

Statement 55. The surgical implant of any of the statements above below statement 35 (or a combination thereof), wherein the body portion comprises a biocompatible material that permits tissue growth therewith.

Statement 56. The surgical implant of any of the statements above below statement 35 (or a combination thereof), further comprising: a bone graft material for application to at least one of the first hole, the second hole, and the interconnected opening.

Statement 57. The surgical implant of any of the statements above below statement 35 (or a combination thereof), wherein the first cavity and the interconnected opening form at an intersection thereof a vertical edge.

Statement 58. The surgical implant of statement 57, wherein the vertical edge has two opposing surfaces, one planar surface along the interconnected opening and one curved surface along the first cavity.

Statement 59. The surgical implant of statement 57, wherein the vertical edge is formed from two opposing curved surfaces.

Statement 60. The surgical implant of statement 57, wherein the vertical edge is formed from two plane opposing surfaces.

Statement 61. The surgical implant of any of the statements above below statement 35 (or a combination thereof), wherein the body portion comprises a cross-shaped solid section extending in a region of the body portion and bounded by four holes in the body portion.

Statement 62. The surgical implant of any of the statements above below statement 35 (or a combination thereof), further comprising intersecting channels formed in the body portion where one of the intersecting channels comprises the interconnected opening.

Statement 63. The surgical implant of statement 62, wherein the intersecting channels connect between four holes in the body portion.

Statement 64. The surgical implant of any of the statements above below statement 35 (or a combination thereof), wherein the body portion comprises a set of regularly spaced six holes with an "X" pattern of interconnection channels between first set of the six holes and with a cross shaped body portion between a second set of the six holes, the set repeating as a unit across the body portion.

Statement 65. The surgical implant of any of the statements above below statement 35 (or a combination thereof), further comprising corrugations formed on an outermost region of the body implant not having any holes therein.

Statement 66. The surgical implant of statement 65, wherein the corrugations comprise teeth on the body portion with diagonal cuts formed therethrough the teeth by the intersecting channels, and optionally the teeth extend above a surface of the body portion containing the first hole and the second hole.

Statement 67. A surgical implant comprising:
a body portion comprising a peripheral section and a central opening extending through the peripheral section;
a plate attached to the peripheral section; and
the plate comprising a first hole formed in an external surface thereof, a second hole adjacent the first hole,
wherein
the first hole has a first sidewall and a first cavity in the body portion,
the second hole has a second sidewall and a second cavity in the body portion, and
the first cavity and the second cavity have an interconnected opening there between.

Statement 68. A kit comprising:
the surgical implant of statement 35 or statement 58; and
an intervertebral insertion device.

Statement 69. A method for securing two bones surfaces together, comprising:
providing between two bone surfaces a porous surface implant having first and second holes with an interconnection there between;
supplying bone graft material into the first and second holes and the interconnection; and
securing the porous surface implant with the bone graft material in place between the two bone surfaces.

Statement 70. A surgical implant comprising:
a body portion comprising a peripheral section and at least one central opening extending through the peripheral section;
the peripheral section comprising a first hole formed in an external surface thereof, a second hole adjacent the first hole,
wherein
the first hole has a first sidewall and a first cavity in the body portion,
the second hole has a second sidewall and a second cavity in the body portion, and
the first cavity and the second cavity have an interconnected opening there between.

Statement 61. The surgical implant of statement 60 having any of the recited elements in statements 36-56 (or a combination thereof) included in the body portion or the peripheral portion.

Statement 62. The surgical implant of statement 60, wherein the body portion includes only the peripheral portion.

Statement 63. The surgical implant of statement 60, wherein the body portion includes a cross connecting member adjoining to side walls.

Statement 64. The surgical implant of statement 63, wherein the peripheral portion abuts the at least one central opening.

Statement 65. A surgical implant comprising:
a body portion comprising a first hole formed in an exterior surface of the body portion, a second hole adjacent the first hole, and at least one through-hole within the body portion and extending entirely thought a depth of the body portion extending entirely thought a depth of the body portion; and
a central opening extending through the body portion,
wherein
the first hole has a first sidewall and a first cavity in the body portion,
the second hole has a second sidewall and a second cavity in the body portion, and
the first cavity and the second cavity have an interconnected opening there between.

Statement 66. The surgical implant of statement 65, wherein the interconnected opening comprises a surface channel formed in the surface of the body portion for interconnecting the first cavity and the second cavity together.

Statement 67. The surgical implant of statement 65 or statement 66, wherein the interconnected opening comprises a vertically-extending slot in at least one of the first sidewall and the second sidewall.

Statement 68. The surgical implant of any of statements 65-67, wherein at least one of the first hole and the second hole comprises a blind hole or a through hole.

Statement 69. The surgical implant of any of statements 65-68, wherein the body portion comprises a cross shaped solid section extending in a region of the body portion having no holes.

Statement 70. The surgical implant of any of statements 65-69, wherein the first cavity and the interconnected opening form at an intersection thereof a surface wall having a vertical edge.

Statement 71. The surgical implant of any of statements 65-70, wherein the body portion comprises a cross-shaped solid section extending in a region of the body portion and bounded by four holes in the body portion.

Statement 72. The surgical implant any of statements 65-71, wherein the body portion comprises a set of regularly spaced six holes with an "X" pattern of interconnection channels between first set of the six holes and with a cross shaped body portion between a second set of the six holes, the set repeating as a unit across the body portion.

Statement 73. The surgical implant of any of statements 65-72, further comprising corrugations formed on the body portion.

Statement 74. The surgical implant of statement 73, wherein the corrugations comprise teeth with diagonal cuts formed therethrough the teeth by the intersecting channels.

Statement 75. The surgical implant of statement 73, wherein the corrugations are formed on an outermost region of the body portion.

Statement 76. The surgical implant of statement 73, wherein the corrugations contain the at least one through-hole.

Statement 77. The surgical implant of any of statements 65-76, wherein the body portion comprises a boundary region and an inner region abutting the central opening.

Statement 78. The surgical implant of statement 77, wherein the boundary region contains the at least one through-hole.

Statement 79. The surgical implant of statement 77, wherein the inner region contains the at least one through-hole.

Statement 80. The surgical implant of statement 77, wherein the boundary region and the inner region contain the at least one through-hole.

Statement 81. The surgical implant of any of statements 65-80, wherein
the central opening comprises two openings, and
the body portion comprises an interconnecting member joining sidewalls of the body portion together, with the interconnecting member disposed between the two openings.

Statement 82. The surgical implant of statement 81, wherein the interconnecting member contains the at least one through-hole.

Statement 83. The surgical implant of any of statements 65-82, wherein the body portion comprises a boundary region abutting the central opening.

Statement 84. The surgical implant of any of statements 65-83, wherein sidewalls of the body portion comprise sidewall openings.

Statement 85. The surgical implant of any of statements 65-84, wherein the at least one through-hole and interconnected openings between blind holes on a top and bottom surface of the body portion are in fluid communication.

Numerous modifications and variations of the present invention are possible in light of the above teachings. It is therefore to be understood that within the scope of the appended claims, the invention may be practiced otherwise than as specifically described herein.

The invention claimed is:

1. A surgical implant comprising:
a body portion defined by a proximal wall, a distal wall, opposing lateral side walls, a top surface and a bottom surface, the body portion configured for insertion between two vertebrae,
the top surface and the bottom surface each and comprising a peripheral portion having corrugations and a central portion adjacent the peripheral portion, the central portion disposed abutting a central opening formed through the body portion;
a plurality of holes formed in the top surface in at least the central portion and a plurality of holes formed in the bottom surface in at least the central portion,
wherein each hole is a blind hole or a through-hole which extends entirely through the body portion from the top surface to the bottom surface; and
at least two interconnecting channels a) formed in each of the top surface and the bottom surface and b) connecting between two adjacent holes of the plurality of holes,
wherein the at least two interconnecting channels in each of the top surface and the bottom surface extend laterally from one of the two adjacent holes to the other of the two adjacent holes in the central portion and extend farther into the peripheral portion of the body portion and cut obliquely across and into sections of the corrugations; and
wherein:
the plurality of holes formed in the top and bottom surfaces each comprise a repeating set of regularly spaced holes,
each repeating set repeats as a unit across the central portion, and
a solid portion is formed between each repeating set by a set of the intersecting channels.

2. The surgical implant of claim 1, wherein the at least two interconnecting channels form a surface wall with a vertical edge, the vertical edge formed by two opposing surfaces, one of the opposing surfaces being planar and another of the opposing surfaces being curved.

3. The surgical implant of claim 1, wherein the at least two interconnecting channels comprise a vertically-extending and a laterally-extending slot formed in the body portion.

4. The surgical implant of claim 1, wherein the solid portion is cross shaped.

5. The surgical implant of claim 1, wherein each repeating set is defined by six regularly spaced holes, and the solid portion is cross-shaped and bounded by four of the six regularly spaced holes.

6. The surgical implant of claim 1, wherein each repeating set comprises six regularly spaced holes with an "X" pattern of the at least two interconnecting channels between a first set of four of the six holes and with the solid portion in a cross shape between a second set of four of the six holes.

7. The surgical implant of claim 1, wherein the corrugations are further formed on the central portion.

8. The surgical implant of claim 1, wherein the corrugations comprise teeth.

9. The surgical implant of claim 7, wherein the corrugations each comprise multiple through-holes.

10. The surgical implant of claim 1, wherein a plurality of through-holes are formed through the peripheral portion.

11. The surgical implant of claim 1, wherein the plurality of holes formed in the top and bottom surfaces comprise through-holes formed only through the central portion.

12. The surgical implant of claim 1, wherein the plurality of holes formed in the top and bottom surfaces comprise through-holes formed through the central portion and the peripheral portion.

13. The surgical implant of claim 1, wherein at least one through-hole of the plurality of holes and at least two of the interconnecting channels connect to a blind hole on each of the top surface and the bottom surface of the body portion.

14. A surgical implant comprising:
a body portion defined by a proximal wall, a distal wall, opposing lateral side walls, a top surface and a bottom surface, the body portion configured for insertion between two vertebrae,
the top surface and the bottom surface each comprising a peripheral portion having corrugations and a central portion adjacent the peripheral portion, the central portion disposed around a central opening formed through the body portion;
a plurality of holes formed in the top surface in at least the central portion and a plurality of holes formed in the bottom surface in at least the central portion,
wherein each hole is a blind hole or a through-hole which extends entirely through the body portion from the top surface to the bottom surface; and
at least two interconnecting channels formed in each of the top surface and the bottom surface, and connecting a through-hole of the plurality of holes to two adjacent other holes of the plurality of holes on each of the top and bottom surfaces, respectively,
wherein the through-hole and the at least two interconnecting channels further connect to a blind holes on each of the top surface and the bottom surface, respectively,
wherein the at least two interconnecting channels in each of the top surface and the bottom surface extend laterally from the two adjacent other holes, respectively, and extend farther into the peripheral portion of the body portion and cut obliquely across and into sections of the corrugations,
and wherein:

the plurality of holes formed in the top and bottom surfaces each comprise a repeating set of regularly spaced holes, each repeating set repeats as a unit across the central portion, and a solid portion is formed between each repeating set by a set of the intersecting channels.

\* \* \* \* \*